(12) United States Patent
Duerr et al.

(10) Patent No.: US 11,787,868 B2
(45) Date of Patent: *Oct. 17, 2023

(54) BISPECIFIC ANTI-HUMAN A-BETA/HUMAN TRANSFERRIN RECEPTOR ANTIBODIES AND METHODS OF USE

(71) Applicant: HOFFMANN-LA ROCHE INC., Little Falls, NJ (US)

(72) Inventors: Harald Duerr, Starnberg (DE); Sebastian Fenn, Achmuehle/Eurasburg (DE); Ulrich Goepfert, Penzberg (DE); Sabine Imhof-Jung, Planegg (DE); Christian Klein, Bonstetten (CH); Laurent Lariviere, Munich (DE); Michael Molhoj, Munich (DE); Joerg Thomas Regula, Munich (DE); Petra Rueger, Penzberg (DE); Wolfgang Schaefer, Mannheim (DE)

(*) Notice: Subject to any disclaimer, the term of this patent is extended or adjusted under 35 U.S.C. 154(b) by 171 days.

This patent is subject to a terminal disclaimer.

(21) Appl. No.: 17/130,477

(22) Filed: Dec. 22, 2020

(65) Prior Publication Data
US 2021/0301030 A1 Sep. 30, 2021
US 2022/0144963 A9 May 12, 2022

Related U.S. Application Data

(60) Division of application No. 15/941,655, filed on Mar. 30, 2018, now Pat. No. 10,941,205, which is a continuation of application No. PCT/EP2016/073411, filed on Sep. 30, 2016.

(30) Foreign Application Priority Data

Oct. 2, 2015 (EP) ..................... 15188064

(51) Int. Cl.
| | |
|---|---|
| C07K 16/28 | (2006.01) |
| C07K 16/18 | (2006.01) |
| C07K 16/46 | (2006.01) |
| A61P 25/28 | (2006.01) |
| A61K 39/00 | (2006.01) |

(52) U.S. Cl.
CPC .......... *C07K 16/2881* (2013.01); *A61P 25/28* (2018.01); *C07K 16/18* (2013.01); *C07K 16/468* (2013.01); *A61K 2039/505* (2013.01); *C07K 2317/31* (2013.01); *C07K 2317/51* (2013.01); *C07K 2317/515* (2013.01); *C07K 2317/52* (2013.01); *C07K 2317/522* (2013.01); *C07K 2317/55* (2013.01); *C07K 2317/56* (2013.01); *C07K 2317/64* (2013.01)

(58) Field of Classification Search
None
See application file for complete search history.

(56) References Cited

U.S. PATENT DOCUMENTS

| | | |
|---|---|---|
| 5,154,924 A | 10/1992 | Friden |
| 5,231,000 A | 7/1993 | Majocha et al. |
| 5,427,927 A | 6/1995 | Meyer et al. |
| 6,008,326 A | 12/1999 | Loosmore et al. |
| 6,015,555 A | 1/2000 | Friden |
| 8,187,594 B2 | 5/2012 | Mather et al. |
| 9,598,496 B2 | 3/2017 | Kurosawa et al. |
| 9,714,292 B2 | 7/2017 | Auer et al. |
| 10,323,089 B2 | 6/2019 | Dengl et al. |
| 10,323,099 B2 | 6/2019 | Bruenker et al. |
| 10,364,292 B2 | 7/2019 | Rueger et al. |
| 10,370,692 B2 | 8/2019 | Kopetzki et al. |
| 10,941,205 B2 | 3/2021 | Duerr et al. |
| 11,098,338 B2 | 8/2021 | Kopetzki et al. |
| 2002/0127652 A1 | 9/2002 | Schambye et al. |
| 2003/0003097 A1 | 1/2003 | Reff et al. |
| 2003/0148404 A1 | 8/2003 | Michaelson |
| 2004/0180417 A1 | 9/2004 | Seidah et al. |
| 2005/0058644 A1 | 3/2005 | Engleman |
| 2005/0142133 A1 | 6/2005 | Azar et al. |
| 2005/0180972 A1 | 8/2005 | Wahl et al. |
| 2006/0008883 A1 | 1/2006 | Lazar et al. |
| 2006/0210557 A1 | 9/2006 | Luisi et al. |
| 2006/0251652 A1 | 11/2006 | Watkins et al. |
| 2008/0167449 A1 | 7/2008 | Azar et al. |
| 2008/0275220 A1* | 11/2008 | Friess .............. A61K 39/39591 530/387.3 |
| 2009/0297436 A1 | 12/2009 | Garcia-Martinez et al. |
| 2009/0297439 A1 | 12/2009 | Comoglio et al. |
| 2010/0016786 A1 | 1/2010 | Drews et al. |
| 2010/0077498 A1* | 3/2010 | Pardridge ............ C07K 14/475 536/23.53 |
| 2010/0121036 A1 | 5/2010 | Fischer et al. |
| 2010/0129357 A1 | 5/2010 | Garcia-Martinez et al. |

(Continued)

FOREIGN PATENT DOCUMENTS

| | | |
|---|---|---|
| EP | 2343086 A2 | 7/2011 |
| EP | 2668901 A1 | 12/2013 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
The extended European Search Report, dated Jun. 21, 2021, in the related European Appl. No. 21151524.2.
The Australian Examination Report, dated Jun. 23, 2022, in the related Australian Appl. No. 2016333510.
The English translation of the Chinese Office Action, dated Feb. 3, 2021, in the related Chinese Appl. No. 201680056850.0.

(Continued)

*Primary Examiner* — Adam Weidner

(57) ABSTRACT

Herein are provided bispecific anti-human A-beta/human transferrin receptor antibodies and methods of using the same.

5 Claims, No Drawings

Specification includes a Sequence Listing.

(56) References Cited

U.S. PATENT DOCUMENTS

| | | |
|---|---|---|
| 2010/0190247 A1 | 7/2010 | Lazar et al. |
| 2012/0141484 A1 | 6/2012 | Garcia-Martinez et al. |
| 2012/0244577 A1 | 9/2012 | Dixit et al. |
| 2013/0034554 A1 | 2/2013 | Garcia-Martinez et al. |
| 2013/0039925 A1 | 2/2013 | Bansal |
| 2013/0090457 A1 | 4/2013 | Cunningham et al. |
| 2013/0177579 A1 | 7/2013 | Lin et al. |
| 2013/0315901 A1 | 11/2013 | Derosier et al. |
| 2014/0212423 A1 | 7/2014 | Hanzatian et al. |
| 2014/0271459 A1 | 9/2014 | Dutzar et al. |
| 2014/0271464 A1 | 9/2014 | Garcia-Martinez et al. |
| 2014/0271661 A1 | 9/2014 | Jin et al. |
| 2015/0030589 A1 | 1/2015 | Goldbach et al. |
| 2015/0132217 A1 | 5/2015 | Chang et al. |
| 2015/0140003 A1 | 5/2015 | Kaluza et al. |
| 2015/0196663 A1* | 7/2015 | Shusta ............ A61K 9/0085 435/254.11 |
| 2015/0266947 A1* | 9/2015 | Sierks ............ C07K 16/005 435/6.12 |
| 2015/0322149 A1 | 11/2015 | Bohrmann et al. |
| 2015/0353639 A1 | 12/2015 | Watts et al. |
| 2016/0145348 A1 | 5/2016 | Stephan |
| 2018/0222992 A1 | 8/2018 | Duerr et al. |
| 2018/0282408 A1 | 10/2018 | Dengl et al. |
| 2018/0291110 A1 | 10/2018 | Klein et al. |
| 2019/0276530 A1 | 9/2019 | Bohrmann et al. |
| 2020/0055931 A1 | 2/2020 | Dengl et al. |
| 2020/0071413 A1 | 3/2020 | Rueger et al. |
| 2020/0216553 A1 | 7/2020 | Seeber et al. |
| 2020/0216554 A1 | 7/2020 | Duerr et al. |

FOREIGN PATENT DOCUMENTS

| | | |
|---|---|---|
| EP | 2787078 A1 | 10/2014 |
| JP | 2017187722 A | 10/2017 |
| RU | 2439160 C1 | 1/2012 |
| WO | 9625088 A1 | 8/1996 |
| WO | 96/39628 A1 | 12/1996 |
| WO | 9639628 A1 | 12/1996 |
| WO | 0023472 A2 | 4/2000 |
| WO | 00/61768 A2 | 10/2000 |
| WO | 2000064482 A1 | 11/2000 |
| WO | 2002002597 A2 | 1/2002 |
| WO | 03/016466 A2 | 2/2003 |
| WO | 2004014953 A2 | 2/2004 |
| WO | 2004020454 A2 | 3/2004 |
| WO | 2004069870 A2 | 8/2004 |
| WO | 2005092925 A2 | 10/2005 |
| WO | 2005116220 A1 | 12/2005 |
| WO | 2006131013 A2 | 12/2006 |
| WO | 2007059782 A1 | 5/2007 |
| WO | 2008/005847 A2 | 1/2008 |
| WO | 2008/025527 A1 | 3/2008 |
| WO | 2008039944 A2 | 4/2008 |
| WO | 2008/063771 A2 | 5/2008 |
| WO | 2008063771 A1 | 5/2008 |
| WO | 2009018411 A1 | 2/2009 |
| WO | 2009040562 A1 | 4/2009 |
| WO | 2009/126616 A2 | 10/2009 |
| WO | 2010102251 A2 | 9/2010 |
| WO | 2010/115551 A1 | 10/2010 |
| WO | 2011066369 A2 | 6/2011 |
| WO | 2011066371 A2 | 6/2011 |
| WO | 2011130377 A2 | 10/2011 |
| WO | 2012093125 A1 | 7/2012 |
| WO | 2013012733 A1 | 1/2013 |
| WO | 2013025853 A1 | 2/2013 |
| WO | 2013/038156 A1 | 3/2013 |
| WO | 2013/039471 A1 | 3/2013 |
| WO | 2013079174 A1 | 6/2013 |
| WO | 2013/113615 A1 | 8/2013 |
| WO | 2013113615 A1 | 8/2013 |
| WO | 2013/127816 A1 | 9/2013 |
| WO | 2014/039855 A1 | 3/2014 |
| WO | 2014/047231 A1 | 3/2014 |
| WO | 2014039855 A1 | 3/2014 |
| WO | 2014047231 A1 | 3/2014 |
| WO | WO 2014033074 * | 3/2014 |
| WO | 2014/052188 A1 | 4/2014 |
| WO | 2014/131711 A1 | 9/2014 |
| WO | 2014131694 A1 | 9/2014 |
| WO | 2014131711 A1 | 9/2014 |
| WO | 2014183973 A1 | 11/2014 |
| WO | 2015/014884 A1 | 2/2015 |
| WO | 2015014884 A1 | 2/2015 |
| WO | 2015063339 A1 | 5/2015 |
| WO | 2015095392 A1 | 6/2015 |
| WO | 2016/020309 A1 | 2/2016 |
| WO | 2016020309 A1 | 2/2016 |
| WO | 2016086189 A2 | 6/2016 |
| WO | 2016166032 A1 | 10/2016 |

OTHER PUBLICATIONS

R&D Systems, "Glial Cell Line-derived Neurotrophic Factor (GDNF)," https://www.rndsystems.com/resources/articles/glial-cell-line-derived-neurotrophic-factor-gdnf, May 14, 2019.

Ulbrich et al., "Transferrin- and transferrin-receptor-antibody-modified nanoparticles enable drug delivery across the blood-brain barrier (BBB)," European Journal of Pharmaceutics and Biopharmaceutics 71, 2009, 251-256.

Pardaidge et al., "Selective Transport of an Anti-transferrin Receptor Antibody through the Blood-Brain Barrier in Vivo," Journal of Pharmacology and Experimental Therapeutics, 1991, vol. 259; Iss. 1, pp. 66-70.

Zhao et al., "Expression, Purification and Activity Analysis of Anti-human Transferrin Receptor ScFv," Chinese Journal of Biotechnology, 22(3),pp. 488-491, May 1, 2006. (English Abstract).

Yan et al., "Soluble Expression and Target Study to Brain of Anti-TfR ScFv," Chinese Journal of Biotechnology, 20(3), pp. 342-247, May 1, 2004. (English Abstract).

Zhai et al., "immunoglobulin heavy chain, partial [Oryctolagus cuniculus]," GenBank: Accession No. AGB75998, Jan. 9, 2013.

Tobinai et al., "A Review of Obinutuzumab (GA101), a Novel Type II Anti-CD20 Monoclonal Antibody, for the Treatment of Patients with B-Cell Malignancies," Adv Ther (2017) 34:324-356.

WHO, "International Nonproprietary Names for Pharmaceutical Substances (INN)," Who Drug Information, vol. 26, No. 4, 2012.

Chen et al., "Modern methods for delivery of drugs across the blood-brain barrier" Advanced Drug Delivery Reviews 64:640-665 ( 2012).

The English translation of the Ukrainian Office Action, dated Dec. 13, 2021, in the related Ukrainian Appl. No. a201804776.

Acton R & D Systems Glial Cell Line-Derived Neurotrophic Factors : Advances in Research and Application 2011 Edition (1996).

Ales Berlec et al., "Current state and recent advances in biopharmaceutical production in *Escherichia coli*, yeasts and mammalian cells" Journal of Industrial Microbiology & Biotechnology 40:257-274 ( 2013).

Arai, R. et al., "Design of the linkers which effectively separate domains of a bifunctional fusion protein" Protein Engineering 14(8):529-532 (2001).

Bien-Ly et al., "Transferrin receptor (TfR) trafficking determines brain uptake of TfR antibody !affinity variants" J Exp. Med. 211(2):233-244 (2014).

Bulbarelli et al., "Trafficking of tail-anchored proteins: transport from the endoplasmic reticulum to the plasma membrane and sorting between surface domains in polarised epithelial cells," Journal of Cell Science 115:1689-1702 (2002).

Chen, X. et al., "Fusion Protein Linkers: Property, Design and Functionality" Adv Drug Deliv Rev 65(10):1357-1369 (Oct. 15, 2013).

Communication Pursuant to Article 94(3) EPC issued by the European Patent Office, dated Sep. 2, 2009, in related European Patent Appl. No. 06 829 502.1.

Comoglio, P. et al., Drug development of MET inhibitors: targeting oncogene addiction and expedience, Nature 73:504-516 (Jun. 2008).

(56) References Cited

OTHER PUBLICATIONS

Di Zenzo, G. et al., "The Intracellular and Extracellular Domains of BP180 Antigen Comprise Novel Epitopes Targeted by Pemphigoid Gestationis Autoantibodies" J. of Investigative Dermatology 127:864-873 (Mar. 19, 2006).
Gulko et al., "Producers, Biology, Selection, Genetic Engineering," Biotechnology 3:3-8 (2000). (English translation.).
Jost et al., "Mammalian Expression and Secretion of Functional Single-chain Fv Molecules," The Journal of Biological Chemistry 269(42):26267-26273 (1994).
Kjeldsen et al., "A removable spacer peptide in an 0-factor-leader/insulin precursor fusion protein improves processing and concomitant yield of the insulin precursor in *Saccharomyces cerevisiae*," Gene 170:107-112 (1996).
Klein C. et al., "Progress in overcoming the chain association issue in bispecific heterodimeric lgG antibodies" MAbs 4(6):653-663 (Jan. 11, 2012).
Guo et al., "Amplification and sequence analysis of the brain derived neurotropic factor (BDNF) gene from the Baiji (Lipotes vexillifer)," Acta Theriologica Sinica 26(1):38-43 (2006). (The English abstract included).
Li et al., "Antibody conjugation via one and two C-terminal selenocysteines" Methods 65:133-138 (2014).
Lim, Y. et al., "Engineering mammalian cells in bioprocessing—current achievements and future perspectives" Biotechnol. Appl. Biochem. 55:175-189 (2010).
Lo et al. et al., "High level expression and secretion of Fc-X fusion proteins in mammalian cells" Protein Eng 11(6):495-500 (1998).
Lu, D. et al., "Acquired antagonistic activity of a bispecific diabody directed against two different epitopes on vascular endothelial growth factor receptor 2" J. of Immunological Methods 230:159-171 (1999).
Meder et al., "Gp135/podocalyxin and NHERF-2 participate in the formation of a preapical domain during polarization of MDCK cells," Journal of Cell Biology 168(2):303-313 (2005).
NCBI_IGF-1_P01343, retrieved on Nov. 4, 2016.
Nestler et al., Molecular Neuropharmacology (Chapter 8),:199, 211-219 (2009).
Palcula, A. et al. "Genetic Analysis of Protein Stability and Function" Annu. Rev. Genet. :23:189-310 (1989).
Perlman et al., "Glycosylation of an N-Terminal Extension Prolongs the Half-Life and Increases the in Vivo Activity of Follicle Stimulating Hormone," The Journal of Clinical Endocrinology & Stimulating Hormone 88(7):3227-3235 (2003).
Seidah et al., "Cellular processing of the nerve growth factor precursor by the mammalian pro-protein convertases," Biochem. J. 314:951-960 (1996).
Shen-Xin et al., "Study on in vitro anti-tumor effect of anti-human transferrin receptor :monoclonal antibody" Chin. J. Cell Mol Immunol (EN-Abstract), 24(2).144-146 (2008). (The English abstract included.).
Supreme People's Court of People's Republic of China Administrative Judgment (2019) Zui Gao Fa Zhi XingZhong No. 235. (The English translation included.).
The Brazilian Preliminary Office Action, dated Nov. 5, 2020, in the related Brazilian Appl. No. BR112018004828-3.
The Brazilian Preliminary Office Action, dated Nov. 5, 2020, in the counter-related Brazilian Appl. No. BR112018004733-3.
The English translation of the Chinese Office Action, dated Nov. 3, 2020, in the related Chinese Patent application No. 201680037169.1.
The English translation of the Ukrainian Office Action, dated Sep. 9, 2020, in the related Ukrainian Patent application No. a 201800597.
The European Office Action, dated Oct. 12, 2020, in the related European Patent Appl. No. 16 774 687.4.
Tobinai et al., "A Review of Obinutuzumab (GA101), a Novel Type II Anti-CD20 Monoclonal Antibody, for the Treatment of Patients with B-Cell Malignancies" Adv Ther 34:324-356 (2017).
Weissmiller et al., "Current advances in using neurotrophic factors to treat neurodegenerative disorders," Translational Neurodegeneration 1(14):1-9 (2012).
WHO Drug Information, "International Nonproprietary Names for Pharmaceutical Substances (INN)," vol. 26, No. 4, 2012 p. 401.
Zhang. J. et al., "Design and optimization of a linker for fusion protein construction" Progress in Natural Science 19(10):1197-1200 (2009).
The English translation of the Ukrainian Office Action, dated Oct. 28, 2022,, in the related Ukrainian Patent application No. a 2020 07290.
Tamura et al., "Structural Correlates of an Anticarcinoma Antibody: Identification of Specificity-Determining Residues (SDRs) and Development of a Minimally Immunogenic Antibody Variant by Retention of SDRs Only," J. Immunol., vol. 164, No. 3, pp. 1432-1441, Feb. 2000.
The New Zealand Office Action, dated Jun. 19, 2023, in the related New Zealand Appl. No. 741067.
Shamenkov D A et al., "Prospects of using apolipoprotein-mediated transport of drugs across the blood-brain barrier for improving pharmacotherapy," Pharmateca, No. 20, pp. 95-98, 2010. (The English abstract included).
The Chinese Office Action, dated Dec. 29, 2018, in the related Chinese Appl. No. 201480069054.1. (The machine- generated translation included.).
The English translation of the Chinese Office Action, dated Oct. 21, 2022, in the related Chinese Patent Application No. 201480069054.1.
R&D Systems, "Gilial Cell Line-derived Neuropathic Factor (GDNF)", originally published in R&D Systems ' 1996 Catalog.
The English translation of the Chinese Office Action, dated Aug. 3, 2023, in the related Chinese Patent Application No. 202111123164.
The English translation of the Chinese Office Action, dated Jan. 14, 2019, in the related Chinese Appl. No. 201480072065.5.
The English translation of the English translation of the Japanese Office Action, dated Jun. 27, 2023, in the related Japanese Appl. No. 2022-084966.
The English translation of the Japanese Office Action, dated Feb. 7, 2019, in the related Japanese Appl. No. 2016-541174.
The English translation of the Japanese Office Action, dated Nov. 20, 2018, in the related Japanese Appl. No. 2016-544800.
The English translation of the Russian Office Action, dated Mar. 27, 2019, in the related Russian Appl. No. 2016128367/10(044271).
The English translation of the Russian Office Action, dated Jul. 20, 2018, in the related Russian Appl. No. 2016128367/10(044271).

\* cited by examiner

SEQUENCE LISTING

```
<160> NUMBER OF SEQ ID NOS: 22

<210> SEQ ID NO 1
<211> LENGTH: 215
<212> TYPE: PRT
<213> ORGANISM: Artificial Sequence
<220> FEATURE:
<223> OTHER INFORMATION: 0015-LC1

<400> SEQUENCE: 1

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 2
<211> LENGTH: 455
<212> TYPE: PRT
<213> ORGANISM: Artificial Sequence
<220> FEATURE:
<223> OTHER INFORMATION: 0015-HC1

<400> SEQUENCE: 2
```

-continued

```
Gln Val Glu Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Asn Ala Ser Gly Thr Arg Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Lys Gly Asn Thr His Lys Pro Tyr Gly Tyr Val Arg Tyr
            100                 105                 110
Phe Asp Val Trp Gly Gln Gly Thr Leu Val Thr Val Ser Ser Ala Ser
        115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Glu Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Glu Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Cys Thr Leu Pro Pro Ser Arg Asp Glu Leu Thr
        355                 360                 365
Lys Asn Gln Val Ser Leu Ser Cys Ala Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Val
                405                 410                 415
Ser Lys Leu Thr Val Asp Lys Ser Arg Trp Gln Gln Gly Asn Val Phe
```

```
                420                 425                 430
Ser Cys Ser Val Met His Glu Ala Leu His Asn His Tyr Thr Gln Lys
        435                 440                 445

Ser Leu Ser Leu Ser Pro Gly
    450                 455

<210> SEQ ID NO 3
<211> LENGTH: 215
<212> TYPE: PRT
<213> ORGANISM: Artificial Sequence
<220> FEATURE:
<223> OTHER INFORMATION: 0015-LC2

<400> SEQUENCE: 3

Ala Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys Ser Ser
                100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys
    210                 215

<210> SEQ ID NO 4
<211> LENGTH: 229
<212> TYPE: PRT
<213> ORGANISM: Artificial Sequence
<220> FEATURE:
<223> OTHER INFORMATION: 0015-Fab

<400> SEQUENCE: 4

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
                20                  25                  30

Met Ser Trp Ile Arg Gln His Pro Gly Lys Gly Leu Glu Trp Ile Gly
            35                  40                  45
```

```
Tyr Ile Trp Ser Gly Gly Ser Thr Asp Tyr Ala Ser Trp Ala Lys Ser
 50                  55                  60

Arg Val Thr Ile Ser Lys Thr Ser Thr Thr Val Ser Leu Lys Leu Ser
 65                  70                  75                  80

Ser Val Thr Ala Ala Asp Thr Ala Val Tyr Tyr Cys Ala Arg Arg Tyr
                 85                  90                  95

Gly Thr Ser Tyr Pro Asp Tyr Gly Asp Ala Ser Gly Phe Asp Pro Trp
                100                 105                 110

Gly Gln Gly Thr Leu Val Thr Val Ser Ser Ala Ser Val Ala Ala Pro
            115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 5
<211> LENGTH: 42
<212> TYPE: PRT
<213> ORGANISM: Homo sapiens

<400> SEQUENCE: 5

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 6
<211> LENGTH: 215
<212> TYPE: PRT
<213> ORGANISM: Artificial Sequence
<220> FEATURE:
<223> OTHER INFORMATION: 0012-LC1

<400> SEQUENCE: 6

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Leu Gln Ile Tyr Asn Met Pro
```

```
                      85                  90                  95
Ile Thr Phe Gly Gln Gly Thr Lys Val Glu Ile Lys Arg Thr Val Ala
                100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 7
<211> LENGTH: 455
<212> TYPE: PRT
<213> ORGANISM: Artificial Sequence
<220> FEATURE:
<223> OTHER INFORMATION: 0012-HC1

<400> SEQUENCE: 7

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
                100                 105                 110

Phe Asp Val Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
```

```
            225                 230                 235                 240
        Pro Glu Leu Leu Gly Gly Pro Ser Val Phe Leu Phe Pro Pro Lys Pro
                        245                 250                 255

Lys Asp Thr Leu Met Ile Ser Arg Thr Pro Glu Val Thr Cys Val Val
                        260                 265                 270

Val Asp Val Ser His Glu Asp Pro Glu Val Lys Phe Asn Trp Tyr Val
                        275                 280                 285

Asp Gly Val Glu Val His Asn Ala Lys Thr Lys Pro Arg Glu Glu Gln
                        290                 295                 300

Tyr Asn Ser Thr Tyr Arg Val Val Ser Val Leu Thr Val Leu His Gln
        305                 310                 315                 320

Asp Trp Leu Asn Gly Lys Glu Tyr Lys Cys Lys Val Ser Asn Lys Ala
                        325                 330                 335

Leu Pro Ala Pro Ile Glu Lys Thr Ile Ser Lys Ala Lys Gly Gln Pro
                        340                 345                 350

Arg Glu Pro Gln Val Cys Thr Leu Pro Pro Ser Arg Asp Glu Leu Thr
                        355                 360                 365

Lys Asn Gln Val Ser Leu Ser Cys Ala Val Lys Gly Phe Tyr Pro Ser
                        370                 375                 380

Asp Ile Ala Val Glu Trp Glu Ser Asn Gly Gln Pro Glu Asn Asn Tyr
        385                 390                 395                 400

Lys Thr Thr Pro Pro Val Leu Asp Ser Asp Gly Ser Phe Phe Leu Val
                        405                 410                 415

Ser Lys Leu Thr Val Asp Lys Ser Arg Trp Gln Gln Gly Asn Val Phe
                        420                 425                 430

Ser Cys Ser Val Met His Glu Ala Leu His Asn His Tyr Thr Gln Lys
                        435                 440                 445

Ser Leu Ser Leu Ser Pro Gly
                        450                 455

<210> SEQ ID NO 8
<211> LENGTH: 229
<212> TYPE: PRT
<213> ORGANISM: Artificial Sequence
<220> FEATURE:
<223> OTHER INFORMATION: 0012-LC2

<400> SEQUENCE: 8

Gln Ser Met Gln Glu Ser Gly Pro Gly Leu Val Lys Pro Ser Gln Thr
        1               5                   10                  15

Leu Ser Leu Thr Cys Thr Val Ser Gly Phe Ser Leu Ser Ser Tyr Ala
                        20                  25                  30

Met Ser Trp Ile Arg Gln His Pro Gly Lys Gly Leu Glu Trp Ile Gly
                        35                  40                  45

Tyr Ile Trp Ser Gly Gly Ser Thr Asp Tyr Ala Ser Trp Ala Lys Ser
        50                  55                  60

Arg Val Thr Ile Ser Lys Thr Ser Thr Val Ser Leu Lys Leu Ser
        65                  70                  75                  80

Ser Val Thr Ala Ala Asp Thr Ala Val Tyr Tyr Cys Ala Arg Arg Tyr
                        85                  90                  95

Gly Thr Ser Tyr Pro Asp Tyr Gly Asp Ala Ser Gly Phe Asp Pro Trp
                        100                 105                 110

Gly Gln Gly Thr Leu Val Thr Val Ser Ser Ala Ser Val Ala Ala Pro
                        115                 120                 125

Ser Val Phe Ile Phe Pro Pro Ser Asp Glu Gln Leu Lys Ser Gly Thr
```

```
            130                 135                 140
Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 9
<211> LENGTH: 688
<212> TYPE: PRT
<213> ORGANISM: Artificial Sequence
<220> FEATURE:
<223> OTHER INFORMATION: 0012-HC2

<400> SEQUENCE: 9

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
```

```
                260                 265                 270
Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Gly Gly Ser Gly Gly Gly Ser Gly
    450                 455                 460

Gly Gly Ser Gly Gly Gly Ser Ala Ile Gln Leu Thr Gln Ser
465                 470                 475                 480

Pro Ser Ser Leu Ser Ala Ser Val Gly Asp Arg Val Thr Ile Thr Cys
                485                 490                 495

Arg Ala Ser Gln Ser Ile Ser Ser Tyr Leu Ala Trp Tyr Gln Gln Lys
            500                 505                 510

Pro Gly Lys Ala Pro Lys Leu Leu Ile Tyr Arg Ala Ser Thr Leu Ala
        515                 520                 525

Ser Gly Val Pro Ser Arg Phe Ser Gly Ser Gly Ser Gly Thr Asp Phe
    530                 535                 540

Thr Leu Thr Ile Ser Ser Leu Gln Pro Glu Asp Phe Ala Thr Tyr Tyr
545                 550                 555                 560

Cys Gln Gln Asn Tyr Ala Ser Ser Asn Val Asp Asn Thr Phe Gly Gly
                565                 570                 575

Gly Thr Lys Val Glu Ile Lys Ser Ser Ala Ser Thr Lys Gly Pro Ser
            580                 585                 590

Val Phe Pro Leu Ala Pro Ser Ser Lys Ser Thr Ser Gly Gly Thr Ala
        595                 600                 605

Ala Leu Gly Cys Leu Val Lys Asp Tyr Phe Pro Glu Pro Val Thr Val
    610                 615                 620

Ser Trp Asn Ser Gly Ala Leu Thr Ser Gly Val His Thr Phe Pro Ala
625                 630                 635                 640

Val Leu Gln Ser Ser Gly Leu Tyr Ser Leu Ser Ser Val Val Thr Val
                645                 650                 655

Pro Ser Ser Ser Leu Gly Thr Gln Thr Tyr Ile Cys Asn Val Asn His
            660                 665                 670

Lys Pro Ser Asn Thr Lys Val Asp Lys Lys Val Glu Pro Lys Ser Cys
        675                 680                 685
```

<210> SEQ ID NO 10
<211> LENGTH: 702
<212> TYPE: PRT
<213> ORGANISM: Artificial Sequence
<220> FEATURE:
<223> OTHER INFORMATION: 0015-HC2

<400> SEQUENCE: 10

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
        355                 360                 365
```

Lys Asn Gln Val Ser Leu Trp Cys Leu Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Gly Gly Ser Gly Gly Gly Ser Gly
450                 455                 460

Gly Gly Ser Gly Gly Gly Ser Gln Ser Met Gln Glu Ser Gly
465                 470                 475                 480

Pro Gly Leu Val Lys Pro Ser Gln Thr Leu Ser Leu Thr Cys Thr Val
                485                 490                 495

Ser Gly Phe Ser Leu Ser Ser Tyr Ala Met Ser Trp Ile Arg Gln His
                500                 505                 510

Pro Gly Lys Gly Leu Glu Trp Ile Gly Tyr Ile Trp Ser Gly Gly Ser
                515                 520                 525

Thr Asp Tyr Ala Ser Trp Ala Lys Ser Arg Val Thr Ile Ser Lys Thr
                530                 535                 540

Ser Thr Thr Val Ser Leu Lys Leu Ser Ser Val Thr Ala Ala Asp Thr
545                 550                 555                 560

Ala Val Tyr Tyr Cys Ala Arg Arg Tyr Gly Thr Ser Tyr Pro Asp Tyr
                565                 570                 575

Gly Asp Ala Ser Gly Phe Asp Pro Trp Gly Gln Gly Thr Leu Val Thr
                580                 585                 590

Val Ser Ser Ala Ser Val Ala Ala Pro Ser Val Phe Ile Phe Pro Pro
                595                 600                 605

Ser Asp Glu Gln Leu Lys Ser Gly Thr Ala Ser Val Val Cys Leu Leu
                610                 615                 620

Asn Asn Phe Tyr Pro Arg Glu Ala Lys Val Gln Trp Lys Val Asp Asn
625                 630                 635                 640

Ala Leu Gln Ser Gly Asn Ser Gln Glu Ser Val Thr Glu Gln Asp Ser
                645                 650                 655

Lys Asp Ser Thr Tyr Ser Leu Ser Ser Thr Leu Thr Leu Ser Lys Ala
                660                 665                 670

Asp Tyr Glu Lys His Lys Val Tyr Ala Cys Glu Val Thr His Gln Gly
                675                 680                 685

Leu Ser Ser Pro Val Thr Lys Ser Phe Asn Arg Gly Glu Cys
690                 695                 700

<210> SEQ ID NO 11
<211> LENGTH: 215
<212> TYPE: PRT
<213> ORGANISM: Artificial Sequence
<220> FEATURE:
<223> OTHER INFORMATION: 0020-LC1

<400> SEQUENCE: 11

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Leu Gln Ile Tyr Asn Met Pro
                 85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 12
<211> LENGTH: 457
<212> TYPE: PRT
<213> ORGANISM: Artificial Sequence
<220> FEATURE:
<223> OTHER INFORMATION: 0020-HC1

<400> SEQUENCE: 12

Gln Val Glu Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Asn Ala Ser Gly Thr Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175
```

-continued

```
His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Cys Thr Leu Pro Pro Ser Arg Asp Glu Leu Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys Gly
    450                 455
```

<210> SEQ ID NO 13
<211> LENGTH: 947
<212> TYPE: PRT
<213> ORGANISM: Artificial Sequence
<220> FEATURE:
<223> OTHER INFORMATION: 0020-HC2

<400> SEQUENCE: 13

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                 85                  90                  95
Ala Arg Gly Lys Gly Asn Thr His Lys Pro Tyr Gly Tyr Val Arg Tyr
             100                 105                 110
Phe Asp Val Trp Gly Gln Gly Thr Leu Val Thr Val Ser Ser Ala Ser
         115                 120                 125
Thr Lys Gly Pro Ser Val Phe Pro Leu Ala Pro Ser Ser Lys Ser Thr
     130                 135                 140
Ser Gly Gly Thr Ala Ala Leu Gly Cys Leu Val Glu Asp Tyr Phe Pro
145                 150                 155                 160
Glu Pro Val Thr Val Ser Trp Asn Ser Gly Ala Leu Thr Ser Gly Val
                 165                 170                 175
His Thr Phe Pro Ala Val Leu Gln Ser Ser Gly Leu Tyr Ser Leu Ser
             180                 185                 190
Ser Val Val Thr Val Pro Ser Ser Ser Leu Gly Thr Gln Thr Tyr Ile
         195                 200                 205
Cys Asn Val Asn His Lys Pro Ser Asn Thr Lys Val Asp Glu Lys Val
     210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                 245                 250                 255
Lys Asp Thr Leu Met Ile Ser Arg Thr Pro Glu Val Thr Cys Val Val
             260                 265                 270
Val Asp Val Ser His Glu Asp Pro Glu Val Lys Phe Asn Trp Tyr Val
         275                 280                 285
Asp Gly Val Glu Val His Asn Ala Lys Thr Lys Pro Arg Glu Glu Gln
     290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                 325                 330                 335
Leu Pro Ala Pro Ile Glu Lys Thr Ile Ser Lys Ala Lys Gly Gln Pro
             340                 345                 350
Arg Glu Pro Gln Val Tyr Thr Leu Pro Pro Cys Arg Asp Glu Leu Thr
         355                 360                 365
Lys Asn Gln Val Ser Leu Trp Cys Leu Val Lys Gly Phe Tyr Pro Ser
     370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                 405                 410                 415
Ser Lys Leu Thr Val Asp Lys Ser Arg Trp Gln Gln Gly Asn Val Phe
             420                 425                 430
Ser Cys Ser Val Met His Glu Ala Leu His Asn His Tyr Thr Gln Lys
         435                 440                 445
Ser Leu Ser Leu Ser Pro Gly Gly Ser Gly Gly Gly Ser Gly
     450                 455                 460
Gly Gly Gly Ser Gly Gly Gly Ser Ala Ile Gln Leu Thr Gln Ser
465                 470                 475                 480
Pro Ser Ser Leu Ser Ala Ser Val Gly Asp Arg Val Thr Ile Thr Cys
                 485                 490                 495
```

```
Arg Ala Ser Gln Ser Ile Ser Ser Tyr Leu Ala Trp Tyr Gln Lys
            500                 505                 510

Pro Gly Lys Ala Pro Lys Leu Leu Ile Tyr Arg Ala Ser Thr Leu Ala
            515                 520                 525

Ser Gly Val Pro Ser Arg Phe Ser Gly Ser Gly Ser Gly Thr Asp Phe
            530                 535                 540

Thr Leu Thr Ile Ser Ser Leu Gln Pro Glu Asp Phe Ala Thr Tyr Tyr
545                 550                 555                 560

Cys Gln Gln Asn Tyr Ala Ser Ser Asn Val Asp Asn Thr Phe Gly Gly
                565                 570                 575

Gly Thr Lys Val Glu Ile Lys Arg Thr Val Ala Ala Pro Ser Val Phe
            580                 585                 590

Ile Phe Pro Pro Ser Asp Glu Gln Leu Lys Ser Gly Thr Ala Ser Val
            595                 600                 605

Val Cys Leu Leu Asn Asn Phe Tyr Pro Arg Glu Ala Lys Val Gln Trp
            610                 615                 620

Lys Val Asp Asn Ala Leu Gln Ser Gly Asn Ser Gln Glu Ser Val Thr
625                 630                 635                 640

Glu Gln Asp Ser Lys Asp Ser Thr Tyr Ser Leu Ser Ser Thr Leu Thr
                645                 650                 655

Leu Ser Lys Ala Asp Tyr Glu Lys His Lys Val Tyr Ala Cys Glu Val
                660                 665                 670

Thr His Gln Gly Leu Ser Ser Pro Val Thr Lys Ser Phe Asn Arg Gly
            675                 680                 685

Glu Cys Gly Gly Gly Gly Ser Gly Gly Gly Gly Ser Gly Gly Gly Gly
            690                 695                 700

Ser Gly Gly Gly Gly Ser Gly Gly Gly Gly Ser Gly Gly Gly Gly Ser
705                 710                 715                 720

Gly Gly Gln Ser Met Gln Glu Ser Gly Pro Gly Leu Val Lys Pro Ser
                725                 730                 735

Gln Thr Leu Ser Leu Thr Cys Thr Val Ser Gly Phe Ser Leu Ser Ser
            740                 745                 750

Tyr Ala Met Ser Trp Ile Arg Gln His Pro Gly Lys Gly Leu Glu Trp
            755                 760                 765

Ile Gly Tyr Ile Trp Ser Gly Gly Ser Thr Asp Tyr Ala Ser Trp Ala
            770                 775                 780

Lys Ser Arg Val Thr Ile Ser Lys Thr Ser Thr Val Ser Leu Lys
785                 790                 795                 800

Leu Ser Ser Val Thr Ala Ala Asp Thr Ala Val Tyr Tyr Cys Ala Arg
                805                 810                 815

Arg Tyr Gly Thr Ser Tyr Pro Asp Tyr Gly Asp Ala Ser Gly Phe Asp
                820                 825                 830

Pro Trp Gly Gln Gly Thr Leu Val Thr Val Ser Ser Ala Ser Thr Lys
            835                 840                 845

Gly Pro Ser Val Phe Pro Leu Ala Pro Ser Ser Lys Ser Thr Ser Gly
            850                 855                 860

Gly Thr Ala Ala Leu Gly Cys Leu Val Lys Asp Tyr Phe Pro Glu Pro
865                 870                 875                 880

Val Thr Val Ser Trp Asn Ser Gly Ala Leu Thr Ser Gly Val His Thr
                885                 890                 895

Phe Pro Ala Val Leu Gln Ser Ser Gly Leu Tyr Ser Leu Ser Ser Val
            900                 905                 910

Val Thr Val Pro Ser Ser Ser Leu Gly Thr Gln Thr Tyr Ile Cys Asn
```

```
                    915                 920                 925
Val Asn His Lys Pro Ser Asn Thr Lys Val Asp Lys Lys Val Glu Pro
    930                 935                 940

Lys Ser Cys
945

<210> SEQ ID NO 14
<211> LENGTH: 215
<212> TYPE: PRT
<213> ORGANISM: Artificial Sequence
<220> FEATURE:
<223> OTHER INFORMATION: 0024-LC1

<400> SEQUENCE: 14

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 455
<212> TYPE: PRT
<213> ORGANISM: Artificial Sequence
<220> FEATURE:
<223> OTHER INFORMATION: 0024-HC1

<400> SEQUENCE: 15

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Asn Ala Ser Gly Thr Arg Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Lys Gly Asn Thr His Lys Pro Tyr Gly Tyr Val Arg Tyr
            100                 105                 110
Phe Asp Val Trp Gly Gln Gly Thr Leu Val Thr Val Ser Ser Ala Ser
            115                 120                 125
Thr Lys Gly Pro Ser Val Phe Pro Leu Ala Pro Ser Ser Lys Ser Thr
130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
            195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
            275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Cys Thr Leu Pro Pro Ser Arg Asp Glu Leu Thr
            355                 360                 365
Lys Asn Gln Val Ser Leu Ser Cys Ala Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Val
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
            435                 440                 445
Ser Leu Ser Leu Ser Pro Gly
450                 455
```

```
<210> SEQ ID NO 16
<211> LENGTH: 215
<212> TYPE: PRT
<213> ORGANISM: Artificial Sequence
<220> FEATURE:
<223> OTHER INFORMATION: 0024-LC2

<400> SEQUENCE: 16

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys
    210                 215

<210> SEQ ID NO 17
<211> LENGTH: 702
<212> TYPE: PRT
<213> ORGANISM: Artificial Sequence
<220> FEATURE:
<223> OTHER INFORMATION: 0024-HC2

<400> SEQUENCE: 17

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
            355                 360                 365

Lys Asn Gln Val Ser Leu Trp Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Gly Ser Gly Gly Gly Gly Ser Gly Gly
        450                 455                 460

Gly Gly Ser Gly Gly Gly Gly Ser Gln Ser Met Gln Glu Ser Gly
465                 470                 475                 480

Pro Gly Leu Val Lys Pro Ser Gln Thr Leu Ser Leu Thr Cys Thr Val
                485                 490                 495

Ser Gly Phe Ser Leu Ser Ser Tyr Ala Met Ser Trp Ile Arg Gln His
            500                 505                 510

Pro Gly Lys Gly Leu Glu Trp Ile Gly Tyr Ile Trp Ser Gly Gly Ser
```

```
                515                 520                 525

Thr Asp Tyr Ala Ser Trp Ala Lys Ser Arg Val Thr Ile Ser Lys Thr
530                 535                 540

Ser Thr Thr Val Ser Leu Lys Leu Ser Ser Val Thr Ala Ala Asp Thr
545                 550                 555                 560

Ala Val Tyr Tyr Cys Ala Arg Arg Tyr Gly Thr Ser Tyr Pro Asp Tyr
                565                 570                 575

Gly Asp Ala Ser Gly Phe Asp Pro Trp Gly Gln Gly Thr Leu Val Thr
                580                 585                 590

Val Ser Ser Ala Ser Val Ala Ala Pro Ser Val Phe Ile Phe Pro Pro
                595                 600                 605

Ser Asp Glu Gln Leu Lys Ser Gly Thr Ala Ser Val Val Cys Leu Leu
610                 615                 620

Asn Asn Phe Tyr Pro Arg Glu Ala Lys Val Gln Trp Lys Val Asp Asn
625                 630                 635                 640

Ala Leu Gln Ser Gly Asn Ser Gln Glu Ser Val Thr Glu Gln Asp Ser
                645                 650                 655

Lys Asp Ser Thr Tyr Ser Leu Ser Ser Thr Leu Thr Leu Ser Lys Ala
                660                 665                 670

Asp Tyr Glu Lys His Lys Val Tyr Ala Cys Glu Val Thr His Gln Gly
                675                 680                 685

Leu Ser Ser Pro Val Thr Lys Ser Phe Asn Arg Gly Glu Cys
690                 695                 700

<210> SEQ ID NO 18
<211> LENGTH: 126
<212> TYPE: PRT
<213> ORGANISM: Homo sapiens

<400> SEQUENCE: 18

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Asn Ala Ser Gly Thr Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
                100                 105                 110

Phe Asp Val Trp Gly Gln Gly Thr Leu Val Thr Val Ser Ser
            115                 120                 125

<210> SEQ ID NO 19
<211> LENGTH: 108
<212> TYPE: PRT
<213> ORGANISM: Homo sapiens

<400> SEQUENCE: 19

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
```

```
                    20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys
            100                 105

<210> SEQ ID NO 20
<211> LENGTH: 122
<212> TYPE: PRT
<213> ORGANISM: Artificial Sequence
<220> FEATURE:
<223> OTHER INFORMATION: 299-023 VH humanization variant_DASG

<400> SEQUENCE: 20

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser
        115                 120

<210> SEQ ID NO 21
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 21

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95
```

```
Val Asp Asn Thr Phe Gly Gly Gly Thr Lys Val Glu Ile Lys
            100                 105                 110
```

<210> SEQ ID NO 22
<211> LENGTH: 760
<212> TYPE: PRT
<213> ORGANISM: Homo sapiens

<400> SEQUENCE: 22

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365
```

```
Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Lys Leu Ala Gln Met
                420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760
```

BISPECIFIC ANTI-HUMAN A-BETA/HUMAN TRANSFERRIN RECEPTOR ANTIBODIES AND METHODS OF USE

CROSS REFERENCE TO RELATED APPLICATIONS

This application is a Divisional Application of U.S. patent application Ser. No. 15/941,655, filed on Mar. 30, 2018, which is a continuation of International Application No. PCT/EP2016/073411 filed on Sep. 30, 2016, which claims benefit of European Patent Application No. 15188064.8, filed on Oct. 2, 2015. Each of prior mentioned applications are hereby incorporated by reference in their entireties.

FIELD OF THE INVENTION

The present invention relates to bispecific antibodies against human A-beta and human transferrin receptor, methods for their production, pharmaceutical compositions containing these antibodies, and uses thereof.

INCORPORATION BY REFERENCE OF SEQUENCE LISTING

This application contains references to amino acids and/or nucleic acid sequences that have been filed concurrently herewith as sequence listing text file "SequenceListing.txt", file size of 68 KB, created on Jun. 16, 2021. The aforementioned sequence listing is hereby incorporated by reference in its entirety pursuant to 37 C.F.R. § 1.52(e)(5).

BACKGROUND

About 70% of all cases of dementia are due to Alzheimer's disease which is associated with selective damage of brain regions and neural circuits critical for cognition. Alzheimer's disease is characterized by neurofibrillary tangles in particular in pyramidal neurons of the hippocampus and numerous amyloid plaques containing mostly a dense core of amyloid deposits and defused halos.

The extracellular neuritic plaques contain large amounts of a pre-dominantly fibrillar peptide termed "amyloid β", "A-beta", "Aβ4", "β-A4" or "Aβ"; see Selkoe, Ann. Rev. Cell Biol. 10 (1994) 373-403; Koo PNAS 96 (1999) 9989-9990; U.S. Pat. No. 4,666,829; Glenner BBRC 12 (1984) 1131). This amyloid is derived from "Alzheimer precursor protein/β-amyloid precursor protein" (APP). APPs are integral membrane glycoproteins (see Sisodia PNAS 89 (1992) 6075) and are endoproteolytically cleaved within the AP sequence by a plasma membrane protease, α-secretase (see Sisodia (1992), Joe. cit.). Furthermore, further secretase activity, in particular β-secretase and γ-secretase activity leads to the extracellular release of amyloid-β (A(3) comprising either 39 amino acids (Aβ 39), 40 amino acids (Aβ 40), 42 amino acids (Aβ 42) or 43 amino acids (Aβ 43) (see Sinha PNAS 96 (1999) 11094-1053; Price, Science 282 (1998) 1078-1083; WO 00/72880 or Hardy, TINS 20 (1997) 154).

It is of note that A-beta has several naturally occurring forms, whereby the human forms are referred to as the above mentioned Aβ39, Aβ40, Aβ41, Aβ42 and Aβ43. The most prominent form, Aβ42, has the amino acid sequence (starting from the N-terminus): DAEFRHDSGYEVHHQKLVF-FAEDVGSNKGAIIGLMVGGVVIA (SEQ ID NO: 05). In Aβ41, Aβ40, Aβ39, the C-terminal amino acids A, IA and VIA are missing, respectively. In the Aβ43-form an additional threonine residue is comprised at the C-terminus of the above depicted sequence.

The time required to nucleate Aβ40 fibrils was shown to be significantly longer than that to nucleate Aβ42 fibrils (see e.g. Lansbury, Jr., P. T. and Harper, J. D., Ann. Rev. Biochem. 66 (1997) 385-407). As reviewed in Wagner (J. Clin. Invest. 104 (1999) 1239-1332) the Aβ42 is more frequently found associated with neuritic plaques and is considered to be more fibrillogenic in vitro. It was also suggested that Aβ42 serves as a "seed" in the nucleation-dependent polymerization of ordered non-crystalline Aβ peptides (see e.g. Jarrett, Cell 93 (1993) 1055-1058). Modified APP processing and/or the generation of extracellular plaques containing proteinaceous depositions are not only known from Alzheimer's pathology but also from subjects suffering from other neurological and/or neurodegenerative disorders. These disorders comprise, inter alia, Down's syndrome, hereditary cerebral hemorrhage with amyloidosis Dutch type, Parkinson's disease, ALS (amyotrophic lateral sclerosis), Creutzfeldt Jacob disease, HIV-related dementia and motor neuropathy.

Until now, only limited medical intervention schemes for amyloid-related diseases have been described. For example, cholinesterase inhibitors like galantamine, rivastigmine or donepezil have been discussed as being beneficial in Alzheimer's patients with only mild to moderate disease. However, also adverse events have been reported due to cholinergic action of these drugs. While these cholinergic-enhancing treatments do produce some symptomatic benefit, therapeutic response is not satisfactory for the majority of patients treated. It has been estimated that significant cognitive improvement occurs in only about 5% of treated patients and there is little evidence that treatment significantly alters the course of this progressive disease.

Consequently, there remains a tremendous clinical need for more effective treatments and in particular those which may arrest or delay progression of the disease. Also NMDA-receptor antagonists, like memantine, have been employed more recently.

However, adverse events have been reported due to the pharmacological activity. Further, such a treatment with these NMDA-receptor antagonists can merely be considered as a symptomatic approach and not a disease-modifying one.

Also immunomodulation approaches for the treatment of amyloid-related disorders have been proposed. WO 99/27944 discloses conjugates that comprise parts of the A-beta peptide and carrier molecules whereby said carrier molecule should enhance an immune response. Another active immunization approach is mentioned in WO 00/72880, wherein also A-beta fragments are employed to induce an immune response.

Also passive immunization approaches with general anti-A-beta antibodies have been proposed in WO 99/27944 or WO 01/62801 and specific humanized antibodies directed against portions of A-beta have been described in WO 02/46237, WO 02/088306 and WO 02/088307. WO 00/77178 describes antibodies binding a transition state adopted by β-amyloid during hydrolysis. WO 03/070760 discloses antibody molecules that recognize two discontinuous amino acid sequences on the A-beta peptide.

WO 2014/033074 relates to blood brain barrier shuttles that bind receptors on the blood brain barrier and methods of using the same. Blood-brain barrier drug delivery of IgG fusion proteins with a transferrin receptor monoclonal antibody have been reported by Pardridge, W. (Exp. Opin. Drug Deliv. 12 (2015) 207-222). Yu, Y. J. et al. (Sci. Translat.

Med. 6 (2014) 261ra154-261ra154) reported that therapeutic bispecific antibodies cross the blood-brain barrier in non-human primates. The disaggregation of amyloid plaque in brain of Alzheimer's disease transgenic mice with daily subcutaneous administration of a tetravalent bispecific antibody that targets the transferrin receptor and the abeta amyloid peptide was reported by Sumbria, R. K., et al. (Mol. Pharm. 10 (2013) 3507-3513). Niewoehner, J., et al. (Neuron 81 (2014) 49-609 reported an increased brain penetration and potency of a therapeutic antibody using a monovalent molecular shuttle.

SUMMARY

Herein is reported a bispecific antibody comprising
a) one (full length) antibody comprising two pairs each of a (full length) antibody light chain and a (full length) antibody heavy chain, wherein the binding sites formed by each of the pairs of the (full length) heavy chain and the (full length) light chain specifically bind to a first antigen, and
b) one additional Fab fragment, wherein the additional Fab fragment is fused to the C-terminus of one of the heavy chains of the (full length) antibody, wherein the binding site of the additional Fab fragment specifically binds to a second antigen,
wherein each of the (full length) antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the (full length) antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the constant light chain domain (CL) and the constant heavy chain domain 1 (CH1) are replaced by each other, and
wherein the first antigen is human A-beta protein and the second antigen is human transferrin receptor.

In one embodiment the additional Fab fragment is fused to the C-terminus of the heavy chain by a peptidic linker.

In one embodiment the N-terminus of the heavy chain variable domain of the Fab fragment is fused to the C-terminus of the full length heavy chain or the C-terminus of the peptidic linker.

In one embodiment
a) the full length heavy chain that is fused to the additional Fab fragments has as C-terminal heavy chain amino acid residues the tripeptide LSP wherein the proline thereof is directly fused to the first amino acid residue of the additional Fab fragment or of the peptidic linker via a peptide bond, and
b) the full length heavy chain that is not fused to the additional Fab fragments has as C-terminal heavy chain amino acid residues the tripeptide LSP, or SPG, or PGK.

In one embodiment the (full length) antibody is
a) a full length antibody of the human subclass IgG1,
b) a full length antibody of the human subclass IgG4,
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain,
f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain,
g) a full length antibody of the human subclass IgG1 with the mutations L234A, L235A, P329G, I253A, H310A and H435A in both heavy chains and the mutations T366W and S354C in one heavy chain and the mutations T366S, L368A, Y407V and Y349C in the respective other heavy chain, or
h) a full length antibody of the human subclass IgG1 with the mutations L234A, L235A, P329G, M252Y, S254T and T256E in both heavy chains and the mutations T366W and S354C in one heavy chain and the mutations T366S, L368A, Y407V and Y349C in the respective other heavy chain.

In one embodiment the (full length) antibody is
a) a full length antibody of the human subclass IgG1,
b) a full length antibody of the human subclass IgG4,
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations i) T366W, and ii) S354C or Y349C, in one heavy chain and the mutations i) T366S, L368A, and Y407V, and ii) Y349C or S354C, in the respective other heavy chain,
f) a full length antibody of the human subclass IgG4 with the mutations S228P, L235E and P329G in both heavy chains and the mutations i) T366W, and ii) S354C or Y349C, in one heavy chain and the mutations i) T366S, L368A, and Y407V, and ii) Y349C or S354C, in the respective other heavy chain,
g) a full length antibody of the human subclass IgG1 with the mutations L234A, L235A, P329G, I253A, H310A and H435A in both heavy chains and the mutations i) T366W, and ii) S354C or Y349C, in one heavy chain and the mutations i) T366S, L368A, and Y407V, and ii) Y349C or S354C, in the respective other heavy chain,
h) a full length antibody of the human subclass IgG1 with the mutations L234A, L235A, P329G, M252Y, S254T and T256E in both heavy chains and the mutations i) T366W, and ii) S354C or Y349C, in one heavy chain and the mutations i) T366S, L368A, and Y407V, and ii) Y349C or S354C, in the respective other heavy chain, or
i) a full length antibody of the human subclass IgG1 with the mutations L234A, L235A, P329G, H310A, H433A and Y436A in both heavy chains and the mutations i) T366W, and ii) S354C or Y349C, in one heavy chain and the mutations i) T366S, L368A, and Y407V, and ii) Y349C or S354C, in the respective other heavy chain.

In one embodiment the additional Fab fragment is fused to the C-terminus of the heavy chain comprising the mutation T366W, or to the C-terminus of the heavy chain comprising the mutations T366S, L368A, and Y407V.

In one embodiment
- the full length antibody is of the human subclass IgG1 with the mutations L234A, L235A and P329G in both heavy chains and the mutations T366W and S354C in one heavy chain and the mutations T366S, L368A, Y407V and Y349C in the respective other heavy chain, and
- the additional Fab fragment is fused to the C-terminus of the heavy chain comprising the mutation T366W, or to the C-terminus of the heavy chain comprising the mutations T366S, L368A, and Y407V.

In one embodiment of all aspects, the human A-beta binding site comprises the VH sequence as in SEQ ID NO: 18, including post-translational modifications of that sequence, and the VL sequence as in SEQ ID NO: 19, including post-translational modifications of that sequence.

In one embodiment of all aspects, the human transferrin receptor binding site comprises the VH sequence as in SEQ ID NO: 20, including post-translational modifications of that sequence, and the VL sequence as in SEQ ID NO: 21, including post-translational modifications of that sequence.

In one embodiment the bispecific antibody comprises
  i) a light chain with an amino acid sequence that has a sequence identity to SEQ ID NO: 01 of 70% or more,
  ii) a heavy chain with an amino acid sequence that has a sequence identity to SEQ ID NO: 02 of 70% or more,
  iii) a light chain with an amino acid sequence that has a sequence identity to SEQ ID NO: 03 of 70% or more, and
  iv) a heavy chain Fab fragment with an amino acid sequence that has a sequence identity to SEQ ID NO: 04 of 70% or more,
wherein
SEQ ID NO: 01 has the amino acid sequence

DIVLTQSPATLSLSPGERATLSCRASQSVSSSYLAWYQQKPGQAPRLL

IYGASSRATGVPARFSGSGSGTDFTLTISSLEPEDFATYYCLQIYNMPIT

FGQGTKVEIKRTVAAPSVFIFPPSDRKLKSGTASVVCLLNNFYPREAK

VQWKVDNALQSGNSQESVTEQDSKDSTYSLSSTLTLSKADYEKHKV

YACEVTHQGLSSPVTKSFNRGEC,

SEQ ID NO: 02 has the amino acid sequence

QVELVESGGGLVQPGGSLRLSCAASGFTFSSYAMSWVRQAPGKGLE

WVSAINASGTRTYYADSVKGRFTISRDNSKNTLYLQMNSLRAEDTAV

YYCARGKGNTHKPYGYVRYFDVWGQGTLVTVSSASTKGPSVFPLAP

SSKSTSGGTAALGCLVEDYFPEPVTVSWNSGALTSGVHTFPAVLQSS

GLYSLSSVVTVPSSSLGTQTYICNVNHKPSNTKVDEKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGKE

YKCKVSNKALPAPIEKTISKAKGQPREPQVCTLPPSRDELTKNQVSLS

CAVKGFYPSDIAVEWESNGQPENNYKTTPPVLDSDGSFFLVSKLTVD

KSRWQQGNVFSCSVMHEALHNHYTQKSLSLSPG,

SEQ ID NO: 03 has the amino acid sequence

AIQLTQSPSSLSASVGDRVTITCRASQSISSYLAWYQQKPGKAPKLLIY

RASTLASGVPSRFSGSGSGTDFTLTISSLQPEDFATYYCQQNYASSNV

DNTFGGGTKVEIKSSASTKGPSVFPLAPSSKSTSGGTAALGCLVKDYF

PEPVTVSWNSGALTSGVHTFPAVLQSSGLYSLSSVVTVPSSSLGTQTY

ICNVNHKPSNTKVDKKVEPKSC, and
SEQ ID NO: 04 has the amino acid sequence

QSMQESGPGLVKPSQTLSLTCTVSGFSLSSYAMSWIRQHPGKGLEWI

GYIWSGGSTDYASWAKSRVTISKTSTTVSLKLSSVTAADTAVYYCAR

RYGTSYPDYGDASGFDPWGQGTLVTVSSASVAAPSVFIFPPSDEQLKS

GTASVVCLLNNFYPREAKVQWKVDNALQSGNSQESVTEQDSKDSTY

SLSSTLTLSKADYEKHKVYACEVTHQGLSSPVTKSFNRGEC.

One aspect as reported herein is a bispecific antibody comprising a (full length) light chain that has the amino acid sequence of SEQ ID NO: 01, a (full length) heavy chain that has the amino acid sequence of SEQ ID NO: 02, a (full length) light chain that has the amino acid sequence of SEQ ID NO: 03, and an antibody Fab fragment comprising the amino acid sequences of SEQ ID NO: 04.

In one embodiment the bispecific antibody is monoclonal.

One aspect as reported herein is an isolated nucleic acid encoding the bispecific antibody as reported herein.

One aspect as reported herein is a host cell comprising the nucleic acid as reported herein encoding the bispecific antibody as reported herein.

One aspect as reported herein is a method of producing a bispecific antibody as reported herein comprising the following steps:
  a) culturing the host cell as reported herein so that the bispecific antibody is produced, and
  b) recovering the bispecific antibody from the cell or the cultivation medium and thereby producing the bispecific antibody as reported herein.

One aspect as reported herein is an immunoconjugate comprising the bispecific antibody as reported herein and a cytotoxic agent.

One aspect as reported herein is a pharmaceutical formulation comprising the bispecific antibody as reported herein and a pharmaceutically acceptable carrier.

One aspect as reported herein is the antibody as reported herein for use as a medicament.

One aspect as reported herein is the bispecific antibody as reported herein for use in treating Alzheimer's disease.

One aspect as reported herein is the bispecific antibody as reported herein for use in inhibiting/slowing down the formation of plaques in the brain.

One aspect as reported herein is the bispecific antibody as reported herein for use in disintegrating β-amyloid plaques.

One aspect as reported herein is the use of the bispecific antibody as reported herein in the manufacture of a medicament.

In one embodiment the medicament is for the treatment of amyloid disorders.

In one embodiment the medicament for the prevention and/or treatment of a disease associated with amyloidogenesis and/or amyloid-plaque formation. In one embodiment the disease is selected from the group consisting of dementia, Alzheimer's disease, motor neuropathy, Down's syndrome, Creutzfeldt Jacob disease, hereditary cerebral hemorrhage with amyloidosis Dutch type, Parkinson's disease, HIV-related dementia, ALS or neuronal disorders related to aging. In one preferred embodiment the medicament is for treatment of Alzheimer's disease.

In one embodiment the medicament is for inhibiting/slowing down the formation of plaques in the brain. In one embodiment the medicament is for medicament for the disintegration of β-amyloid plaques.

One aspect as reported herein is a method of treating an individual having a disease associated with amyloidogenesis and/or amyloid-plaque formation comprising administering to the individual an effective amount of the bispecific antibody as reported herein.

One aspect as reported herein is a method of treating an individual having Alzheimer's disease comprising administering to the individual an effective amount of the bispecific antibody as reported herein.

One aspect as reported herein is a method for the disintegration of β-amyloid plaques in the brain of an individual comprising administering to the individual an effective amount of the bispecific antibody as reported herein to disintegrate β-amyloid plaques in the brain.

One aspect as reported herein is a method of inhibiting/slowing down the formation of plaques in the brain of an individual comprising administering to the individual an effective amount of the bispecific antibody as reported herein to inhibit/slow down the formation of plaques in the brain.

DETAILED DESCRIPTION OF EMBODIMENTS OF THE INVENTION

The knobs into holes dimerization modules and their use in antibody engineering are described in Carter P.; Ridgway J. B. B.; Presta L. G.: Immunotechnology, Volume 2, Number 1, February 1996, pp. 73-73. The additional disulfide bridge in the CH3 domain is reported in Merchant, A. M., et al., Nat. Biotechnol. 16 (1998) 677-681.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

I. Definitions

The "blood-brain-barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal-cord barrier within the spinal cord, and the blood-retinal-barrier within the retina are contiguous capillary barriers within the CNS, and are herein collectively referred to an the blood-brain-barrier or BBB. The BBB also encompasses the blood-CSF barrier (choroid plexus) where the barrier is comprised of ependymal cells rather than capillary endothelial cells.

The terms "anti-human A-beta antibody" and "an antibody specifically binding to human A-beta" refer to an antibody that is capable of binding the human A-beta peptide with sufficient affinity such that the antibody is useful as a diagnostic and/or therapeutic agent in targeting A-beta peptide.

It is of note that human A-beta has several naturally occurring forms, whereby the human forms are referred to as Aβ39, Aβ40, Aβ41, Aβ42 and Aβ43. The most prominent form, Aβ42, has the amino acid sequence of SEQ ID NO: 05. In Aβ41, Aβ40, Aβ39, the C-terminal amino acids A, IA and VIA are missing, respectively. In the Aβ43 form an additional threonine residue is comprised at the C-terminus of SEQ ID NO: 05. In one embodiment the human A-beta protein has the amino acid sequence of SEQ ID NO: 05.

Thus, the term also encompasses antibodies that bind to a shortened fragment of the human A-beta polypeptide.

The "central nervous system" or "CNS" refers to the complex of nerve tissues that control bodily function, and includes the brain and spinal cord.

A "blood-brain-barrier receptor" (abbreviated "BBBR" herein) is an extracellular membrane-linked receptor protein expressed on brain endothelial cells which is capable of transporting molecules across the BBB or be used to transport exogenous administrated molecules. Examples of BBBR herein include: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). One preferred BBBR is transferrin receptor (TfR).

The "transferrin receptor" ("TfR") is a transmembrane glycoprotein (with a molecular weight of about 180,000 Da) composed of two disulphide-bonded sub-units (each of apparent molecular weight of about 90,000 Da) involved in iron uptake in vertebrates. In one embodiment, the TfR as mentioned herein is human TfR comprising the amino acid sequence as in Schneider et al (Nature 311 (1984) 675-678), for example. In one embodiment the human transferrin receptor has the amino acid sequence of SEQ ID NO: 22.

A "multispecific antibody" denotes an antibody having binding specificities for at least two different epitopes on the same antigen or two different antigens. Exemplary multispecific antibodies may bind both a BBBR and a brain antigen. Multispecific antibodies can be prepared as full-length antibodies or antibody fragments (e.g. F(ab')$_2$ bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, and multispecific antibodies (e.g., bispecific antibodies) so long as they exhibit the desired antigen-binding activity.

The term "antibody-dependent cellular cytotoxicity (ADCC)" is a function mediated by Fc receptor binding and refers to lysis of target cells by an antibody as reported herein in the presence of effector cells. ADCC is measured in one embodiment by the treatment of a preparation of CD19 expressing erythroid cells (e.g. K562 cells expressing recombinant human CD19) with an antibody as reported herein in the presence of effector cells such as freshly isolated PBMC (peripheral blood mononuclear cells) or purified effector cells from buffy coats, like monocytes or NK (natural killer) cells. Target cells are labeled with $^{51}Cr$ and subsequently incubated with the antibody. The labeled cells are incubated with effector cells and the supernatant is analyzed for released $^{51}Cr$. Controls include the incubation of the target endothelial cells with effector cells but without the antibody. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

The term "complement-dependent cytotoxicity (CDC)" refers to lysis of cells induced by the antibody as reported herein in the presence of complement. CDC is measured in one embodiment by the treatment of CD19 expressing human endothelial cells with an antibody as reported herein in the presence of complement.

The cells are in one embodiment labeled with calcein. CDC is found if the antibody induces lysis of 20% or more of the target cells at a concentration of 30 μg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate (6)]).

"Effector functions" refer to those biological activities attributable to the Fc region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4

(1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

An "effective amount" of an agent, e.g., a pharmaceutical formulation, refers to an amount effective, at dosages and for periods of time necessary, to achieve the desired therapeutic or prophylactic result.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA. The term "no binding of FcγR" denotes that at an antibody concentration of 10 μg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R.L., et al. J. Biol. Chem. 276 (2001) 6591-6604; Lund, J., et al., FASEB J. 9 (1995) 115-119; Morgan, A., et al., Immunology 86 (1995) 319-324; and EP 0 307 434). In one embodiment the antibody as reported herein is of IgG1 or IgG2 subclass and comprises the mutation PVA236, GLPSS331, and/or L234A/L235A. In one embodiment the antibody as reported herein is of IgG4 subclass and comprises the mutation L235E. In one embodiment the antibody further comprises the mutation S228P.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

The antibodies as reported herein comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat; Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A (numbering according to EU index of Kabat).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody," and "whole antibody" are used herein interchangeably to refer to an antibody having a structure substantially similar to a native antibody structure or having heavy chains that contain an Fc region as defined herein. A "full length antibody" is an antibody that comprises a light and heavy chain antigen-binding variable region (VL, VH) as well as a light chain constant domain (CL) and heavy chain constant domains, CH1, CH2 and CH3. The constant domains may be native sequence constant domains (e.g. human native sequence constant domains) or amino acid sequence variants thereof. In more detail a full length antibody comprises two antibody light chains (each comprising a light chain variable domain and a light chain constant domain) and two antibody heavy chains (each comprising a heavy chain variable domain, a hinge region and the heavy chain constant domains CH1, CH2 and CH3). The C-terminal amino acid residues K or GK may be present or not independently of each other in the two antibody heavy chains of a full length antibody. Also a full length antibody may comprise amino acid additions, mutations and deletions within the domains but not the deletion of an entire domain.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human A-beta/human transferrin receptor antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies as reported herein are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W. H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that the bispecific anti-human A-beta/human transferrin receptor antibody as reported herein has improved properties. In certain embodiments, bispecific anti-human A-beta/human transferrin receptor antibodies are provided. Antibodies as reported herein are useful, e.g., for the diagnosis or treatment of Alzheimer's disease.

A. Exemplary Bispecific Anti-Human A-Beta/Human Transferrin Receptor Antibodies

In one aspect, the invention provides isolated bispecific antibodies that bind to human A-beta and human transferrin receptor. The antibodies are bispecific antibodies consisting of a full length core antibody and a fused Fab fragment in which certain domains are crosswise exchanged. Thus, the resulting bispecific antibody is asymmetric. Therefore, the bispecific antibody is produced using the heterodimerization technology called knobs-into-holes using a first heavy chain with the so-called knob mutations (HCknob) and a second heavy chain with the so-called hole mutations (HChole).

Antibody 0012, which is also an aspect of the current invention, is composed of four polypeptides that have the amino acid sequence of SEQ ID NO: 06 to 09.

Antibody 0012 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the light chain variable domain (VL) and the heavy chain variable domain (VH) are replaced by each other, and
wherein the first antigen is human A-beta protein and the second antigen is human transferrin receptor.

Antibody 0015, which is also an aspect of the current invention, is composed of four polypeptides that have the amino acid sequence of SEQ ID NO: 01 to 03 and SEQ ID NO: 10.

Antibody 0015 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

Antibody 0020, which is also an aspect of the current invention, is composed of three polypeptides that have the amino acid sequence of SEQ ID NO: 11 to 13.

Antibody 0020 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen is a single chain Fab fragment, and wherein the first antigen is human A-beta protein and the second antigen is human transferrin receptor.

Antibody 0024, which is also an aspect of the current invention, is composed of four polypeptides that have the amino acid sequence of SEQ ID NO: 14 to 17.

Antibody 0024 is a bispecific antibody comprising a) one full length antibody comprising two pairs each of a full length antibody light chain and a full length antibody heavy chain, wherein the binding sites formed by each of the pairs of the full length heavy chain and the full length light chain specifically bind to a first antigen, and b) one additional Fab fragment, wherein the additional Fab fragment is fused to the C-terminus of one heavy chain of the full length antibody, wherein the binding site of the additional Fab fragment specifically binds to a second antigen, wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

Different allocation/combination of the respective polypeptides on different expression plasmids and different ratios of the resulting plasmids have been used for the recombinant production of the bispecific antibodies. The results are presented in the following Table.

| | | relative peak area [%] (CE-SDS; non-reduced analysis) | | | |
|---|---|---|---|---|---|
| antibody | plasmid ratio | LC | ½ mAb hole | hole-hole chain dimer | antibody monomer |
| 0012 | 1(HChole + LC):3(HCknob + LCcross) | | 12 | 9 | 78 |
| 0012 | 1(LC):1(HChole + LC): 3(HCknob + LCcross) | 1 | 9 | 9 | 79 |
| 0012 | 1(LC + HChole):3(Hcknob + LC):1(LCcross) | 6 | 9 | 9 | 75 |
| 0015 | 1(HChole + LC):3(HCknob + LCcross) | | 7 | 23 | 62 |
| 0015 | 1(LC):1(HChole + LC): 3(HCknob + LCcross) | 4 | 17 | 75 | |
| 0015 | 1(LC + HChole):3(Hcknob + LC):1(LCcross) | 4 | 20 | 66 | |
| 0020 | 1(HChole + LC):4(HCknob + LCcross) | | 16 | 11 | 72 |

The bispecific antibodies have been produced in small scale and the by-product distribution has been analyzed after a first purification step using a protein A affinity chromatography and after the second purification step using a preparative size-exclusion chromatography. The results are presented in the following Table.

| | | harvest 3 liter fermentation after preparative protein A product monomer (CE-SDS not red./yield) | by-product distribution (CE-SDS not red.) | | |
|---|---|---|---|---|---|
| antibody | plasmid ratio | | LC | ½ mAb hole | hole-hole dimer + ¾ mAb |
| 0012 | 1:1:3 | 65% 13.3 mg | 3% | 28% | 35% |
| 0024 | 1:1:3 | 70% 14.8 mg | 6% | 15% | 7% |
| 0015 | 1:1:3 | 85% 15.8 mg | 4% | 5% | 5% |
| 0020 | 1:4 | 29% 6 mg | 11% | 44% | 8% |

| | | harvest 3 liter fermentation after preparative protein A and preparative SEC product monomer (CE-SDS not red./yield) | by-product distribution (CE-SDS not red.) | | |
|---|---|---|---|---|---|
| antibody | plasmid ratio | | LC | ½ mAb hole | hole-hole dimer + ¾ mAb |
| 0012 | 1:1:3 | >90% 2.8 mg | 5% | 3% | 2.5% |
| 0024 | 1:1:3 | 78% 4 mg | 11% | 5% | 6% |
| 0015 | 1:1:3 | >95% 5.8 mg | 1% | 0.5% | 1% |
| 0020 | 1:4 | 68% 0.8 mg | 13% | 10% | 8.6% |

| antibody | plasmid ratio | harvest 3l after preparative protein A purification monomer by SEC | by-products SEC [%] HMW | by-products SEC [%] LMW | end product by SEC | by-products SEC [%] HMW | by-products SEC [%] LMW |
|---|---|---|---|---|---|---|---|
| 0012 | 1:1:3 | 78% | 0 | 22 | 97.5% | 0 | 2.5 |
| 0024 | 1:1:3 | 80% | 0 | 20 | 96% | 0 | 4 |
| 0015 | 1:1:3 | 87% | 0 | 13 | 97% | 0 | 3 |
| 0020 | 1:4 | 53% | 7 | 40 | 97% | 0 | 3 |

The anti-A-beta binding site comprises an additional glycosylation site. Therefore the glycosylation has been determined. The results are presented in the following Table.

| | | HChole | | HCknob | |
|---|---|---|---|---|---|
| | | CE-SDS; reduced; rel. peak area [%] | | | |
| antibody | plasmid ratio | non-glyc. | glyc. | non-glyc. | glyc. |
| 0012 | 1(HChole + LC): 3(HCknob + LCcross) | 10 | 14 | 8 | 18 |
| 0012 | 1(LC):1(HChole + LC): 3(HCknob + LCcross) | 9 | 13 | 8 | 21 |
| 0012 | 1(LC + HChole): 3(Hcknob + LC): 1(LCcross) | 10 | 13 | 7 | 18 |
| 0015 | 1(HChole + LC): 3(HCknob + LCcross) | 7 | 16 | 5 | 25 |

-continued

Percentage of non-glycosylated Fab in 3 liter fermentations after ProtA purification

| antibody | plasmid ratio | HChole | | HCknob | |
|---|---|---|---|---|---|
| | | CE-SDS; reduced; rel. peak area [%] | | | |
| | | non-glyc. | glyc. | non-glyc. | glyc. |
| 0015 | 1(LC):1(HChole + LC):3(HCknob + LCcross) | 6 | 16 | 5 | 29 |
| 0015 | 1(LC + HChole):3(Hcknob + LC):1(LCcross) | 7 | 15 | 6 | 26 |
| 0020 | 1(HChole + LC):4(HCknob + LCcross) | 9 | 18 | 7 | 21 |

| antibody | plasmid ratio | HChole | | HCknob | |
|---|---|---|---|---|---|
| | | CE-SDS; reduced | | | |
| | | non-glyc. | glyc. | non-glyc. | glyc. |
| 0012 | 1(LC):1(HChole + LC):3(HCknob + LCcross) | 23 | 77 | 10 | 90 |
| 0015 | 1(LC):1(HChole + LC):3(HCknob + LCcross) | 16 | 84 | 8 | 92 |
| 0024 | 1(LC):1(HChole + LC):3(HCknob + LCcross) | 16 | 84 | 7.5 | 92.5 |

Percentage of non-glycosylated Fab in 3l fermentations after ProtA+SEC purification

| antibody | plasmid ratio | HChole | | HCknob | |
|---|---|---|---|---|---|
| | | CE-SDS; reduced | | | |
| | | non-glyc. | glyc. | non-glyc. | glyc. |
| 0012 | 1(LC):1(HChole + LC):3(HCknob + LCcross) | 8 | 92 | 6 | 94 |
| 0015 | 1(LC):1(HChole + LC):3(HCknob + LCcross) | 10 | 90 | 4.5 | 95.5 |
| 0024 | 1(LC):1(HChole + LC):3(HCknob + LCcross) | 8 | 92 | 4.5 | 95.5 |

The stability of the bispecific antibodies has been tested by incubation for 14 day at specific pH values in buffer. The results are presented in the following Table.

| parameter | | antibody 0012 | antibody 0015 | antibody 0024 |
|---|---|---|---|---|
| relative A-beta peptide (1-40) binding by BIAcore | 14 days, pH 6.0, 40° C., His/NaCl buffer | 87% | 96% | 97% |
| | 14 days, pH 7.4, 37° C., PBS buffer | 82% | 86% | 101% |
| relative human transferrin receptor binding by BIAcore | 14 days, pH 6.0, 40° C., His/NaCl buffer | 101% | 91% | 93% |
| | 14 days, pH 7.4, 37° C., PBS buffer | 78% | 85% | 90% |

The aggregation temperature for antibody 0015 and 0024 was determined to be approx. 53-55° C. and for antibody 0012 to be approx. 54-56° C.

The off-rate ($k_d$ in [1/Ms]) for the binding to the human transferrin receptor as determined by BIAcore was comparable for antibodies 0015 and 0024 as well as for the parental anti-human transferrin receptor antibody at 25° C., 37° C. and 40° C.: 1.86E-02 to 1.97E-02, 1.98E-2 to 2.03E-2 and 1.44E-02, respectively.

The A-beta specific effector function of all antibodies were comparable to the parental monospecific anti-A-beta antibody in a U937-cell assay. The data is presented in the following Table.

| antibody | IL-8 [ng/ml] | IP-10 [ng/ml] |
|---|---|---|
| parental anti-A-beta antibody | 5 | 4.3 |
| antibody-0012 | 7 | 5.3 |
| antibody-0015 | — | 5 |
| antibody-0020 | 7 | 4.5 |
| antibody-0024 | 8 | 5.2 |

None of the bispecific antibodies showed neutrophil activation in vitro.

Overall antibody 0015 showed suitable properties and is therefore the preferred aspect of the invention. Furthermore this antibody has improved properties, which lie, amongst others, in the improved side-product profile.

In one aspect herein is provided a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

Another aspect as reported herein is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the constant light chain domain (CL) and the constant heavy chain domain 1 (CH1) are replaced by each other,
wherein the first antigen is human A-beta protein and the second antigen is human transferrin receptor,
wherein the human A-beta binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18 and a light chain variable domain (VL) sequence having at least 90%, 91%, 92%, 93%, 94%, 95%, 96%, 97%, 98%, 99%, or 100% sequence identity to the amino acid sequence of SEQ ID NO: 19, and
wherein the human transferrin receptor binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20 and a light chain variable domain (VL) sequence having at least 90%, 91%, 92%, 93%, 94%, 95%, 96%, 97%, 98%, 99%, or 100% sequence identity to the amino acid sequence of SEQ ID NO: 21.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 18 or 20. In certain embodiments, substitutions, insertions, or deletions occur in regions outside the HVRs (i.e., in the FRs).

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 19 or 21. In certain embodiments, substitutions, insertions, or deletions occur in regions outside the HVRs (i.e., in the FRs).

In one embodiment, the human A-beta binding site comprises the VH sequence as in SEQ ID NO: 18, including post-translational modifications of that sequence, and the VL sequence as in SEQ ID NO: 19, including post-translational modifications of that sequence.

In one embodiment, the human transferrin receptor binding site comprises the VH sequence as in SEQ ID NO: 20, including post-translational modifications of that sequence, and the VL sequence as in SEQ ID NO: 21, including post-translational modifications of that sequence.

In one embodiment the bispecific antibody comprises
i) a light chain that has a sequence identity to SEQ ID NO: 01 of 70-100%, at least 70%, at least 80%, at least 90%, or 95% or more,
ii) a heavy chain that has a sequence identity to SEQ ID NO: 02 of 70-100%, at least 70%, at least 80%, at least 90%, or 95% or more,
iii) a light chain that has a sequence identity to SEQ ID NO: 03 of 70-100%, at least 70%, at least 80%, at least 90%, or 95% or more, and
iv) a heavy chain Fab fragment that has a sequence identity to SEQ ID NO: 04 of 70-100%, at least 70%, at least 80%, at least 90%, or 95% or more,
wherein
SEQ ID NO: 01 has the amino acid sequence

DIVLTQSPATLSLSPGERATLSCRASQSVSSSYLAWYQQKPGQAPRLL

IYGASSRATGVPARFSGSGSGTDFTLTISSLEPEDFATYYCLQIYNMPIT

FGQGTKVEIKRTVAAPSVFIFPPSDRKLKSGTASVVCLLNNFYPREAK

VQWKVDNALQSGNSQESVTEQDSKDSTYSLSSTLTLSKADYEKHKV

YACEVTHQGLSSPVTKSFNRGEC,

SEQ ID NO: 02 has the amino acid sequence

QVELVESGGGLVQPGGSLRLSCAASGFTFSSYAMSWVRQAPGKGLE

WVSAINASGTRTYYADSVKGRFTISRDNSKNTLYLQMNSLRAEDTAV

YYCARGKGNTHKPYGYVRYFDVWGQGTLVTVSSASTKGPSVFPLAP

SSKSTSGGTAALGCLVEDYFPEPVTVSWNSGALTSGVHTFPAVLQSS

GLYSLSSVVTVPSSSLGTQTYICNVNHKPSNTKVDEKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGKE

YKCKVSNKALPAPIEKTISKAKGQPREPQVCTLPPSRDELTKNQVSLS

CAVKGFYPSDIAVEWESNGQPENNYKTTPPVLDSDGSFFLVSKLTVD

KSRWQQGNVFSCSVMHEALHNHYTQKSLSLSPG,

SEQ ID NO: 03 has the amino acid sequence

AIQLTQSPSSLSASVGDRVTITCRASQSISSYLAWYQQKPGKAPKLLIY

RASTLASGVPSRFSGSGSGTDFTLTISSLQPEDFATYYCQQNYASSNV

DNTFGGGTKVEIKSSASTKGPSVFPLAPSSKSTSGGTAALGCLVKDYF

PEPVTVSWNSGALTSGVHTFPAVLQSSGLYSLSSVVTVPSSSLGTQTY

ICNVNHKPSNTKVDKKVEPKSC, and

SEQ ID NO: 04 has the amino acid sequence

QSMQESGPGLVKPSQTLSLTCTVSGFSLSSYAMSWIRQHPGKGLEWI

GYIWSGGSTDYASWAKSRVTISKTSTTVSLKLSSVTAADTAVYYCAR

RYGTSYPDYGDASGFDPWGQGTLVTVSSASVAAPSVFIFPPSDEQLKS

GTASVVCLLNNFYPREAKVQWKVDNALQSGNSQESVTEQDSKDSTY

SLSSTLTLSKADYEKHKVYACEVTHQGLSSPVTKSFNRGEC.

Another aspect as reported herein is a bispecific antibody comprising
  a) one full length antibody comprising two pairs each of a full length antibody light chain and a full length antibody heavy chain, wherein the binding sites formed by each of the pairs of the full length heavy chain and the full length light chain specifically bind to a first antigen, and
  b) one additional Fab fragment, wherein the additional Fab fragment is fused to the C-terminus of one heavy chain of the full length antibody, wherein the binding site of the additional Fab fragment specifically binds to a second antigen,
  wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
  wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
  wherein the additional Fab fragment specifically binding to the second antigen comprises a domain crossover such that the constant light chain domain (CL) and the constant heavy chain domain 1 (CH1) are replaced by each other, wherein the first antigen is human A-beta protein and the second antigen is human transferrin receptor,
  wherein the human A-beta binding site comprises a heavy chain variable domain (VH) that has the amino acid sequence of SEQ ID NO: 18 and a light chain variable domain (VL) that has the amino acid sequence of SEQ ID NO: 19, and
  wherein the human transferrin receptor binding site comprises a heavy chain variable domain (VH) that has the amino acid sequence of SEQ ID NO: 20 and a light chain variable domain (VL) that has the amino acid sequence of SEQ ID NO: 21.

Another aspect as reported herein is a bispecific antibody comprising
  a) one full length antibody comprising two pairs each of a full length antibody light chain and a full length antibody heavy chain, wherein the binding sites formed by each of the pairs of the full length heavy chain and the full length light chain specifically bind to a first antigen, wherein the full length antibody comprises an Fc-region that is formed by the Fc-region polypeptides, each comprising the CH1, CH2 and CH3 domain, of the two full length heavy chains, and
  b) one additional Fab fragment, wherein the additional Fab fragment is fused to the C-terminus of one heavy chain of the full length antibody, wherein the binding site of the additional Fab fragment specifically binds to a second antigen,
  wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
  wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
  wherein the additional Fab fragment specifically binding to the second antigen comprises a domain crossover such that the constant light chain domain (CL) and the constant heavy chain domain 1 (CH1) are replaced by each other,
  wherein the first antigen is human A-beta protein and the second antigen is human transferrin receptor,
  wherein the human A-beta binding site comprises a heavy chain variable domain (VH) that has the amino acid sequence of SEQ ID NO: 18 and a light chain variable domain (VL) that has the amino acid sequence of SEQ ID NO: 19,
  wherein the human transferrin receptor binding site comprises a heavy chain variable domain (VH) that has the amino acid sequence of SEQ ID NO: 20 and a light chain variable domain (VL) that has the amino acid sequence of SEQ ID NO: 21, and
  wherein the Fc-region polypeptides are
  a) of the human subclass IgG1,
  b) of the human subclass IgG4,
  c) of the human subclass IgG1 with the mutations L234A, L235A and P329G,
  d) of the human subclass IgG4 with the mutations S228P, L235E and P329G,
  e) of the human subclass IgG1 with the mutations L234A, L235A and P329G in both Fc-region polypeptides and the mutations T366W and S354C in one Fc-region polypeptide and the mutations T366S, L368A, Y407V and Y349C in the respective other Fc-region polypeptide,
  f) of the human subclass IgG4 with the mutations S228P and P329G in both Fc-region polypeptides and the mutations T366W and S354C in one Fc-region polypeptide and the mutations T366S, L368A, Y407V and Y349C in the respective other Fc-region polypeptide,
  g) of the human subclass IgG1 with the mutations L234A, L235A, P329G, I253A, H310A and H435A in both Fc-region polypeptides and the mutations T366W and S354C in one Fc-region polypeptide and the mutations T366S, L368A, Y407V and Y349C in the respective other Fc-region polypeptide,
  h) of the human subclass IgG1 with the mutations L234A, L235A, P329G, M252Y, S254T and T256E in both Fc-region polypeptides and the mutations T366W and S354C in one Fc-region polypeptide and the mutations T366S, L368A, Y407V and Y349C in the respective other Fc-region polypeptide, or i) a full length antibody of the human subclass IgG1 with the mutations L234A, L235A, P329G, H310A, H433A and Y436A in both heavy chains and the mutations i) T366W, and ii) S354C or Y349C, in one heavy chain and the mutations i) T366S, L368A, and Y407V, and ii) Y349C or S354C, in the respective other heavy chain.

In a further aspect, a bispecific anti-human A-beta/human transferrin receptor antibody according to any of the above embodiments may incorporate any of the features, singly or in combination, as described in Sections 1-3 below:

1. Chimeric and Humanized Antibodies

In certain embodiments, an antibody provided herein is a chimeric antibody. Certain chimeric antibodies are described, e.g., in U.S. Pat. No. 4,816,567; and Morrison, S.L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S.V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

2. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 35.57-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

3. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, herein is contemplated an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wisc.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No.7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding a bispecific anti-human A-beta/human transferrin receptor antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making a bispecific anti-human A-beta/human transferrin receptor antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of a bispecific anti-human A-beta/human transferrin receptor antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR$^-$CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Methods and Compositions for Diagnostics and Detection

In certain embodiments, any of the bispecific anti-human A-beta/human transferrin receptor antibodies provided herein are useful for detecting the presence of A-beta in a biological sample. The term "detecting" as used herein encompasses quantitative or qualitative detection. In certain embodiments, a biological sample comprises a cell or tissue.

In one embodiment, a bispecific anti-human A-beta/human transferrin receptor antibody for use in a method of diagnosis or detection is provided. In a further aspect, a method of detecting the presence of A-beta in a biological sample is provided. In certain embodiments, the method comprises contacting the biological sample with a bispecific anti-human A-beta/human transferrin receptor antibody as described herein under conditions permissive for binding of the bispecific anti-human A-beta/human transferrin receptor antibody to A-beta, and detecting whether a complex is formed between the bispecific anti-human A-beta/human transferrin receptor antibody and A-beta. Such method may be an in vitro or in vivo method.

In certain embodiments, labeled bispecific anti-human A-beta/human transferrin receptor antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, ruceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Pharmaceutical Formulations

Pharmaceutical formulations of a bispecific anti-human A-beta/human transferrin receptor antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration are generally sterile. Sterility may be readily accomplished, e.g., by filtration through sterile filtration membranes. In one embodiment the formulation is isotonic.

E. Therapeutic Methods and Compositions

Any of the bispecific anti-human A-beta/human transferrin receptor antibodies provided herein may be used in therapeutic methods.

In one aspect, a bispecific anti-human A-beta/human transferrin receptor antibody for use as a medicament is provided. In further aspects, a bispecific anti-human A-beta/human transferrin receptor antibody for use in preventing and/or treating a disease associated with amyloidogenesis and/or amyloid-plaque formation is provided. In certain embodiments, a bispecific anti-human A-beta/human transferrin receptor antibody for use in a method of treatment is provided. In certain embodiments, herein is provided a bispecific anti-human A-beta/human transferrin receptor antibody for use in a method of treating an individual having a disease associated with amyloidogenesis and/or amyloid-plaque formation comprising administering to the individual an effective amount of the bispecific anti-human A-beta/human transferrin receptor antibody. In one such embodiment, the method further comprises administering to the individual an effective amount of at least one additional therapeutic agent, such as listed below or an anti-pTau or an anti-alpha-synuclein antibody. In further embodiments, herein is provided a bispecific anti-human A-beta/human transferrin receptor antibody for use in inhibiting the formation of plaques and/or disintegrating β-amyloid plaques. In certain embodiments, herein is provided a bispecific anti-human A-beta/human transferrin receptor antibody for use in a method of inhibiting the formation of plaques and/or disintegrating β-amyloid plaques in an individual comprising administering to the individual an effective of the bispecific anti-human A-beta/human transferrin receptor antibody to inhibit the formation of plaques and/or to disintegrate β-amyloid plaques. An "individual" according to any of the above embodiments is preferably a human.

In a further aspect, herein is provided the use of a bispecific anti-human A-beta/human transferrin receptor antibody in the manufacture or preparation of a medicament. In one embodiment, the medicament is for treatment of a disease associated with amyloidogenesis and/or amyloid-plaque formation. In a further embodiment, the medicament is for use in a method of treating a disease associated with amyloidogenesis and/or amyloid-plaque formation comprising administering to an individual having a disease associated with amyloidogenesis and/or amyloid-plaque formation an effective amount of the medicament. In one such embodiment, the method further comprises administering to the individual an effective amount of at least one additional therapeutic agent, such as listed below or an anti-pTau or an anti-alpha synuclein antibody. In a further embodiment, the medicament is for the inhibition of the formation of plaques and/or the disintegration of β-amyloid plaques. In a further embodiment, the medicament is for use in a method of inhibiting the formation of plaques and/or the disintegration of β-amyloid plaques in an individual comprising administering to the individual an amount effective of the medicament to inhibit the formation of plaques and/or to disintegrate β-amyloid plaques. An "individual" according to any of the above embodiments may be a human.

In a further aspect, herein is provided a method for treating a disease associated with amyloidogenesis and/or amyloid-plaque formation. In one embodiment, the method comprises administering to an individual having a disease associated with amyloidogenesis and/or amyloid-plaque formation an effective amount of a bispecific anti-human A-beta/human transferrin receptor antibody. In one such embodiment, the method further comprises administering to the individual an effective amount of at least one additional therapeutic agent, such as given below or an anti-pTau or an anti-alpha-synuclein antibody. An "individual" according to any of the above embodiments may be a human.

In a further aspect, herein is provided a method for inhibiting the formation of plaques and/or for disintegrating β-amyloid plaques in an individual. In one embodiment, the method comprises administering to the individual an effective amount of a bispecific anti-human A-beta/human transferrin receptor antibody to inhibit the formation of plaques and/or to disintegrate β-amyloid plaques. In one embodiment, an "individual" is a human.

In a further aspect, herein are provided pharmaceutical formulations comprising any of the bispecific anti-human A-beta/human transferrin receptor antibodies provided herein, e.g., for use in any of the above therapeutic methods. In one embodiment, a pharmaceutical formulation comprises any of the bispecific anti-human A-beta/human transferrin receptor antibodies provided herein and a pharmaceutically acceptable carrier. In another embodiment, a pharmaceutical formulation comprises any of the bispecific anti-human A-beta/human transferrin receptor antibodies provided herein and at least one additional therapeutic agent, e.g., as given below or an anti-pTau or an anti-alpha-synuclein antibody.

Antibodies as reported herein can be used either alone or in combination with other agents in a therapy. For instance, an antibody as reported herein may be co-administered with at least one additional therapeutic agent. In certain embodiments, an additional therapeutic agent is a therapeutic agent effective to treat the same or a different neurological disorder as the bispecific antibody as reported herein is being employed to treat. Exemplary additional therapeutic agents include, but are not limited to: the various neurological drugs described above, cholinesterase inhibitors (such as donepezil, galantamine, rovastigmine, and tacrine), NMDA receptor antagonists (such as memantine), amyloid beta peptide aggregation inhibitors, antioxidants, γ-secretase modulators, nerve growth factor (NGF) mimics or NGF gene therapy, PPARy agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicrotinic receptor modulators, active or passive amyloid beta peptide immunization, phosphodiesterase inhibitors, serotonin receptor antagonists and anti-amyloid beta peptide antibodies. In certain embodiments, the at least one additional therapeutic agent is selected for its ability to mitigate one or more side effects of the neurological drug.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of the bispecific anti-human A-beta/human transferrin receptor antibody and administration of an additional therapeutic agent occur within about one month, or within about one, two or three weeks, or within about one, two, three, four, five, or six days, of each other. Antibodies as reported herein can also be used in combination with other interventional therapies such as, but not limited to, radiation therapy, behavioral therapy, or other therapies known in the art and appropriate for the neurological disorder to be treated or prevented.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Lipid-based methods of transporting the fusion construct or a compound across the BBB include, but are not limited to, encapsulating the fusion construct or a compound in liposomes that are coupled to monovalent binding entity that bind to receptors on the vascular endothelium of the BBB (see e.g., US 2002/0025313), and coating the monovalent binding entity in low-density lipoprotein particles (see e.g., US 2004/0204354) or apolipoprotein E (see e.g., US 2004/0131692).

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate as reported herein in place of or in addition to a bispecific anti-human A-beta/human transferrin receptor antibody.

III. Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody as reported herein. The label or package insert indicates that the composition is used for treating the condition of choice. Moreover, the article of manufacture may comprise (a) a first container with a composition contained therein, wherein the composition comprises an antibody as reported herein; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to a bispecific antibody as reported herein.

IV. Examples

The following are examples of methods and compositions of the invention. It is understood that various other embodiments may be practiced, given the general description provided above.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to numbering according to Kabat (Kabat, E. A., et al., Sequences of Proteins of Immunological Interest, 5th ed., Public Health Service, National Institutes of Health, Bethesda, Md. (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The long gene segments, which were flanked by singular restriction endonuclease cleavage sites, were assembled by annealing and ligating oligonucleotides including PCR amplification and subsequently cloned via the indicated restriction sites. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described bispecific antibodies, expression plasmids for transient expression (e.g. in HEK293 cells) based either on a cDNA organization with or without a CMV-intron A promoter or on a genomic organization with a CMV promoter can be applied.

Beside the antibody expression cassette the vectors contain:

an origin of replication which allows replication of this plasmid in *E. coli*, and a β-lactamase gene which confers ampicillin resistance in *E. coli*.

The transcription unit of the antibody gene is composed of the following elements:

unique restriction site(s) at the 5' end the immediate early enhancer and promoter from the human cytomegalovirus, the intron A sequence in the case of cDNA organization, a 5'-untranslated region derived from a human antibody gene, an immunoglobulin heavy chain signal sequence, the respective antibody chain encoding nucleic acid either as cDNA or with genomic exon-intron organization, a 3' untranslated region with a polyadenylation signal sequence, and unique restriction site(s) at the 3' end.

The fusion genes encoding the antibody chains are generated by PCR and/or gene synthesis and assembled by known recombinant methods and techniques by connection of the according nucleic acid segments e.g. using unique restriction sites in the respective vectors. The subcloned nucleic acid sequences are verified by DNA sequencing. For transient transfections larger quantities of the plasmids are prepared by plasmid preparation from transformed *E. coli* cultures (Nucleobond AX, Macherey-Nagel).

For all constructs knob-into-hole heterodimerization technology was used with a typical knob (T366W) substitution in the first CH3 domain and the corresponding hole substitutions (T366S, L368A and Y407V) in the second CH3 domain (as well as two additional introduced cysteine residues S354C/Y349'C) (contained in the respective corresponding heavy chain (HC) sequences depicted above).

Cell Culture Techniques

Standard cell culture techniques as described in Current Protocols in Cell Biology (2000), Bonifacino, J. S., Dasso, M., Harford, J. B., Lippincott-Schwartz, J. and Yamada, K. M. (eds.), John Wiley & Sons, Inc., are used.

Transient Transfections in HEK293-F System

The bispecific antibodies are produced by transient expression. Therefore a transfection with the respective plasmids using the HEK293-F system (Invitrogen) according to the manufacturer's instruction is done. Briefly, HEK293-F cells (Invitrogen) growing in suspension either in a shake flask or in a stirred fermenter in serum-free FreeStyle™ 293 expression medium (Invitrogen) are transfected with a mix of the respective expression plasmids and 293fectin™ or fectin (Invitrogen). For 2 L shake flask (Corning) HEK293-F cells are seeded at a density of $1.0*10^6$ cells/mL in 600 mL and incubated at 120 rpm, 8% $CO_2$. On the next day the cells are transfected at a cell density of approx. $1.5*10^6$ cells/mL with approx. 42 mL of a mixture of A) 20 mL Opti-MEM medium (Invitrogen) comprising 600 µg total plasmid DNA (1 µg/mL) and B) 20 ml Opti-MEM medium supplemented with 1.2 mL 293 fectin or fectin (2 µl/mL). According to the glucose consumption glucose solution is added during the course of the fermentation. The supernatant containing the secreted antibody is harvested after 5-10 days and antibodies are either directly purified from the supernatant or the supernatant is frozen and stored.

Protein Determination

The protein concentration of purified antibodies and derivatives was determined by determining the optical density (OD) at 280 nm, using the molar extinction coefficient calculated on the basis of the amino acid sequence according to Pace, et al., Protein Science 4 (1995) 2411-1423.

Antibody Concentration Determination in Supernatants

The concentration of antibodies and derivatives in cell culture supernatants was estimated by immunoprecipitation with protein A agarose-beads (Roche Diagnostics GmbH, Mannheim, Germany). Therefore, 60 µL protein A Agarose beads were washed three times in TBS-NP40 (50 mM Tris buffer, pH 7.5, supplemented with 150 mM NaCl and 1% Nonidet-P40). Subsequently, 1-15 mL cell culture supernatant was applied to the protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche Diagnostics GmbH, Mannheim, Germany) and briefly four times with 0.5 mL 100 mM Na-citrate buffer (pH 5.0). Bound antibody was eluted by addition of 35 µl NuPAGE® LDS sample buffer (Invitrogen). Half of the sample was combined with NuPAGE® sample reducing agent or left unreduced, respectively, and heated for 10 min at 70° C. Consequently, 5-30 µl were applied to a 4-12% NuPAGE® Bis-Tris SDS-PAGE gel (Invitrogen) (with MOPS buffer for non-reduced SDS-PAGE and MES buffer with NuPAGE® antioxidant running buffer additive (Invitrogen) for reduced SDS-PAGE) and stained with Coomassie Blue.

The concentration of the antibodies in cell culture supernatants was quantitatively measured by affinity HPLC chromatography. Briefly, cell culture supernatants containing antibodies that bind to protein A were applied to an Applied Biosystems Poros A/20 column in 200 mM $KH_2PO_4$, 100 mM sodium citrate, pH 7.4 and eluted with 200 mM NaCl, 100 mM citric acid, pH 2.5 on an Agilent HPLC 1100 system. The eluted antibody was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Streptavidin A-96 well microtiter plates (Roche Diagnostics GmbH, Mannheim, Germany) were coated with 100 µL/well biotinylated anti-human IgG capture molecule F(ab')2<h-Fcγ>BI (Dianova) at 0.1 µg/mL for 1 hour at room temperature or alternatively overnight at 4° C. and subsequently washed three times with 200 µL/well PBS, 0.05% Tween (PBST, Sigma). Thereafter, 100 µL/well of a dilution series in PBS (Sigma) of the respective antibody containing cell culture supernatants was added to the wells and incubated for 1-2 hour on a shaker at room temperature. The wells were washed three times with 200 µL/well PBST and bound antibody was detected with 100 µl F(ab')2<hFcγ>POD (Dianova) at 0.1 µg/mL as the detection antibody by incubation for 1-2 hours on a shaker at room temperature. Unbound detection antibody was removed by washing three times with 200 µL/well PBST. The bound detection antibody was detected by addition of 100 µL ABTS/well followed by incubation. Determination of absorbance was performed on a Tecan Fluor Spectrometer at a measurement wavelength of 405 nm (reference wavelength 492 nm).

Preparative Antibody Purification

Antibodies were purified from filtered cell culture supernatants referring to standard protocols. In brief, antibodies were applied to a protein A Sepharose column (GE healthcare) and washed with PBS. Elution of antibodies was achieved at pH 2.8 followed by immediate neutralization. Aggregated protein was separated from monomeric antibodies by size exclusion chromatography (Superdex 200, GE Healthcare) in PBS or in 20 mM Histidine buffer comprising 150 mM NaCl (pH 6.0). Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® antioxidant running buffer additive) or MOPS (non-reduced gels) running buffer was used.

CE-SDS

Purity and antibody integrity were analyzed by CE-SDS using microfluidic Labchip technology (PerkinElmer, USA). Therefore, 5 µl of antibody solution was prepared for CE-SDS analysis using the HT Protein Express Reagent Kit according manufacturer's instructions and analyzed on LabChip GXII system using a HT Protein Express Chip. Data were analyzed using LabChip GX Software.

Analytical Size Exclusion Chromatography

Size exclusion chromatography (SEC) for the determination of the aggregation and oligomeric state of antibodies was performed by HPLC chromatography. Briefly, protein A purified antibodies were applied to a Tosoh TSKgel G3000SW column in 300 mM NaCl, 50 mM $KH_2PO_4$/$K_2HPO_4$ buffer (pH 7.5) on an Dionex Ultimate® system (Thermo Fischer Scientific), or to a Superdex 200 column (GE Healthcare) in 2×PBS on a Dionex HPLC-System. The eluted antibody was quantified by UV absorbance and integration of peak areas. BioRad Gel Filtration Standard 151-1901 served as a standard.

Mass Spectrometry

This section describes the characterization of the bispecific antibodies with emphasis on their correct assembly. The expected primary structures were analyzed by electrospray ionization mass spectrometry (ESI-MS) of the deglycosylated intact antibody and in special cases of the deglycosylated/limited LysC digested antibody.

The antibodies were deglycosylated with N-Glycosidase F in a phosphate or Tris buffer at 37° C. for up to 17 h at a protein concentration of 1 mg/ml. The limited LysC (Roche Diagnostics GmbH, Mannheim, Germany) digestions were performed with 100 µg deglycosylated antibody in a Tris buffer (pH 8) at room temperature for 120 hours, or at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Chemical Degradation Test

Samples were split into three aliquots and re-buffered into 20 mM His/His*HCl, 140 mM NaCl, pH 6.0 or into PBS, respectively, and stored at 40° C. (His/NaCl) or 37° C. (PBS). A control sample was stored at −80° C.

After incubation ended, samples were analyzed for relative active concentration (BIAcore), aggregation (SEC) and fragmentation (capillary electrophoresis or SDS-PAGE) and compared with the untreated control.

Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffin oil. The hydrodynamic radius was measured repeatedly by dynamic light scattering on a DynaPro Plate Reader (Wyatt) while the samples were heated with a rate of 0.05° C./min from 25° C. to 80° C.

Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim1000) starts to increase.

Alternatively, samples were transferred in a 9 μL multi-cuvette array. The multi-cuvette array was heated from 35° C. to 90° C. at a constant rate of 0.1° C./minute in an Optim1000 instrument (Avacta Analytical Inc.). The instrument continuously records the intensity of scattered light of a 266 nm laser with a data point approximately every 0.5° C. Light scattering intensities were plotted against the temperature. The aggregation onset temperature (T_agg) is defined as the temperature at which the scattered light intensity begins to increase.

The melting temperature is defined as the inflection point in fluorescence intensity vs. wavelength graph Example 1

Expression and Purification

The bispecific antibodies were produced as described above in the general materials and methods section.

The bispecific antibodies were purified from the supernatant by a combination of protein A affinity chromatography and size exclusion chromatography. The obtained products were characterized for identity by mass spectrometry and analytical properties such as purity by CE-SDS, monomer content and stability.

The expected primary structures were analyzed by electrospray ionization mass spectrometry (ESI-MS) of the deglycosylated intact antibody and deglycosylated/plasmin digested or alternatively deglycosylated/limited LysC digested antibody as described in the general methods section.

Additional analytical methods (e.g. thermal stability, mass spectrometry and functional assessment) were only applied after protein A and SEC purification.

Example 2

Determination of Binding to Aβ1-40 Fibers In Vitro by ELISA

Binding of the bispecific antibodies to fibrillar Aβ is measured by an ELISA assay. Briefly, Aβ(1-40) is coated at 7 μg/mL in PBS onto Maxisorb plates for 3 days at 37° C. to produce fibrillar Abeta, and then dried for 3 h at RT. The plate is blocked with 1% CroteinC and 0.1% RSA in PBS (blocking buffer) for 1 h at RT, then washed once with wash buffer. Bispecific antibodies or controls are added at concentrations up to 100 nM in blocking buffer and incubated at 4° C. overnight. After 4 wash steps, constructs are detected by addition of anti-human-IgG-HRP (Jackson Immunoresearch) at 1:10,000 dilution in blocking buffer (1 RT), followed by 6 washes and incubation in TMB (Sigma). Absorbance is read out at 450 nm after stopping color development with 1 N HCl.

Example 3

Determination of Binding to Transferrin Receptor In Vitro

Binding of the bispecific antibodies to murine transferrin receptor is tested by FACS analysis on mouse X63.AG8-563 myeloma cells. If the Aβ antibody shows a certain tendency to non-specifically bind to Ag8 cells, specific binding can be quantified by co-incubation with a 20 fold excess of anti-mouse-TfR antibody. Cells are harvested by centrifugation, washed once with PBS and $5 \times 10^4$ cells incubated with a 1.5 pM to 10 nM dilution series of the polypeptide fusions with or without addition of 200 nM anti-mouse TfR antibody in 100 μL RPMI/10% FCS for 1.5 h on ice. After 2 washes with RPMI/10% FCS, cells are incubated with goat-anti-human IgG coupled to Phycoerythrin (Jackson Immunoresearch) at a dilution of 1:600 in RPMI/19% FCS for 1.5 h on ice. Cells are again washed, resuspended in RPMI/10% FCS and Phycoerythrin fluorescence measured on a FACS-Array instrument (Becton-Dickinson).

Example 4

Surface Plasmon Resonance-Based Binding Assay for Human TfR-Antibody Interaction The binding experiment were carried out on a BIAcore B 4000 (GE Healthcare) equipped with C1 sensor chip (GE Healthcare, cat.no. BR1005-35) pre-treated with anti-human Fab antibody (GE Healthcare, cat.no 28-9583-25) using a standard amine coupling chemistry procedure accordingly to the vendor's manual.

For kinetic measurements the sample antibody was immobilized applying a contact time of 60 seconds and a flow rate of 10 μL/min in phosphate buffer saline pH 7.4, 0.05% Tween 20 at 25° C. Recombinant His6-tagged human transferrin receptor (R&D systems, cat.no 2474-TR-050) was applied in increasing concentrations and the signal monitored over the time. An average time span of 150 seconds of association time and 600 seconds of dissociation time at 30 μL/min flow rate was recorded. Data were fit using a 1:1 binding model (Langmuir isotherm).

Example 5

Staining of Native Human β-amyloid Plaques from Brain Sections of an Alzheimer's Disease Patient by Indirect Immunofluorescence using a Bispecific Antibody as Reported Herein The bispecific antibodies can be tested for the ability to stain native human β-amyloid plaques by immunohistochemistry analysis using indirect immunofluorescence. Specific and sensitive staining of genuine human β-amyloid plaques can be demonstrated. Cryostat sections of unfixed tissue from the temporal cortex obtained postmortem from patients positively diagnosed for Alzheimer's disease are labeled by indirect immunofluorescence. A two-step incubation is used to detect bound bispecific antibody, which is revealed by affinity-purified goat anti-human (GAH555) IgG (H+L) conjugated to Alexa 555 dye (Molecular Probes). Controls can include unrelated human IgG1 antibodies (Sigma) and the secondary antibody alone, which all should give negative results.

Example 6

In Vivo β-amyloid Plaque Decoration by a Bispecific Antibody as Reported Herein in a Mouse Model of Alzheimer's Disease Bispecific antibody can be tested in APP/PS2 double transgenic mice, a mouse model for AD-related amyloidosis (Richards, J. Neuroscience, 23 (2003) 8989-9003) for their ability to immuno-decorate β-amyloid plaques in vivo. This enabled assessment of the extent of brain penetration and binding to amyloid-β plaques. The fusion polypeptide can be administered at different doses compared to naked anti-Aβ monoclonal antibody and after 6 days animals are perfused with phosphate-buffered saline and the brains frozen on dry ice and prepared for cryosectioning.

The presence of the antibodies bound to β-amyloid plaques can be assessed using unfixed cryostat sections either by single-labeled indirect immunofluorescence with goat anti-human IgG (H+L) conjugated to Alexa555 dye (GAH555) (Molecular Probes) at a concentration of 15 μg/ml for 1 hour at room temperature. A counterstaining for amyloid plaques can be done by incubation with BAP-2, a mouse monoclonal antibody against Aβ conjugated to Alexa 488 at a concentration of 0.5 μg/ml for 1 hour at room temperature. Slides are embedded with fluorescence mounting medium (S3023 Dako) and imaging is done by confocal laser microscopy.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A bispecific antibody specifically binding to human A-beta protein and human transferrin receptor, comprising:
   a first light chain of SEQ ID NO: 01 or that has a sequence identity to SEQ ID NO: 01 of at least 90%;
   a first heavy chain of SEQ ID NO: 02 or that has a sequence identity to SEQ ID NO: 02 of at least 90%;
   a second light chain of SEQ ID NO: 03 or that has a sequence identity to SEQ ID NO: 03 of at least 90%; and
   a second heavy chain of SEQ ID NO: 10 or that has a sequence identity to SEQ ID NO: 10 of at least 90%,
   wherein substitutions, insertions, or deletions occur in regions outside hypervariable regions.

2. The bispecific antibody according to claim 1, wherein the bispecific antibody is monoclonal.

3. A pharmaceutical formulation, comprising the bispecific antibody according to claim 1 and a pharmaceutically acceptable carrier.

4. A method of treating Alzheimer's disease in an individual, comprising the step of administering an effective amount of the bispecific antibody according to claim 1 to said individual in need thereof.

5. A method of inhibiting or slowing down the formation of plaques in the brain of an individual, comprising the step of administering an effective amount of the bispecific antibody according to claim 1 to said individual in need thereof.

* * * * *

UNITED STATES PATENT AND TRADEMARK OFFICE
CERTIFICATE OF CORRECTION

| | | |
|---|---|---|
| PATENT NO. | : 11,787,868 B2 | Page 1 of 1 |
| APPLICATION NO. | : 17/130477 | |
| DATED | : October 17, 2023 | |
| INVENTOR(S) | : Harald Duerr | |

It is certified that error appears in the above-identified patent and that said Letters Patent is hereby corrected as shown below:

On the Title Page

At item (60), please delete "Division of application No. 15/941,655, filed on Mar. 30, 2018, now Pat. No. 10,941,205, which is a continuation of application No. PCT/EP2016/073411, filed on Sep. 30, 2016." and add -- Continuation of application No. 15/941,655, filed on Mar. 30, 2018, now Pat. No. 10,941,205, which is a continuation of application No. PCT/EP2016/073411, filed on Sep. 30, 2016. --

Signed and Sealed this
Sixteenth Day of December, 2025

John A. Squires
*Director of the United States Patent and Trademark Office*